(12) United States Patent
Lanzavecchia

(10) Patent No.: US 8,124,092 B2
(45) Date of Patent: Feb. 28, 2012

(54) ANTIBODIES AGAINST H5N1 STRAINS OF INFLUENZA A VIRUS

(75) Inventor: Antonio Lanzavecchia, Bellinzona (CH)

(73) Assignee: Institute for Research in Biomedicine, Bellinzona (CH)

( * ) Notice: Subject to any disclaimer, the term of this patent is extended or adjusted under 35 U.S.C. 154(b) by 811 days.

(21) Appl. No.: 12/048,040

(22) Filed: Mar. 13, 2008

(65) Prior Publication Data

US 2010/0278834 A1 Nov. 4, 2010

Related U.S. Application Data

(60) Provisional application No. 60/894,612, filed on Mar. 13, 2007.

(51) Int. Cl.
*C07K 16/10* (2006.01)
*A61K 39/42* (2006.01)

(52) U.S. Cl. ............... 424/147.1; 530/388.1; 530/387.3; 530/388.15; 530/388.3; 424/133.1; 424/135.1

(58) Field of Classification Search ........................ None
See application file for complete search history.

(56) References Cited

FOREIGN PATENT DOCUMENTS

| WO | 02/46235 | 6/2002 |
|---|---|---|
| WO | 2007/021002 | 2/2007 |
| WO | 2007/031550 A2 | 3/2007 |
| WO | 2007/031550 A3 | 3/2007 |
| WO | 2007/052242 | 5/2007 |
| WO | 2007/089753 | 8/2007 |
| WO | 2007/134327 | 11/2007 |
| WO | 2008/028946 | 3/2008 |
| WO | 2008/033105 A1 | 3/2008 |
| WO | 2008/033105 C1 | 3/2008 |
| WO | 2008/033159 | 3/2008 |

OTHER PUBLICATIONS

Paul Fundamental Immunology $3^{rd}$ 1993, pp. 242, 292-295.*
Rudikoff PNAS vol. 79 pp. 1979-9183 1982.*
Coleman Reasearch Immunology 1994 vol. 145, pp. 33-36.*
Casset Biochem Biophys Research Com 2003, vol. 307, pp. 198-205.*
Corbeil et al 1996 Vaccine vol. 14, pp. 521-525.*
Sigal et al., The Journal of Immunology 1987 vol. 139, pp. 1985-1990.*
Brendon J. Hanson; Passive immunoprophylaxis and therapy with humanized monoclonal antibody specific for influenza A H5 hemagglutinin in mice; Published: Oct. 14, 2006.

* cited by examiner

*Primary Examiner* — Mary E Mosher
*Assistant Examiner* — Myron Hill
(74) *Attorney, Agent, or Firm* — Dennis A. Bennett; Suman Mirmira

(57) ABSTRACT

Provided are human antibodies that can neutralize a H5N1 strain of influenza A virus. Also provided are antibodies that can neutralize a strain of influenza A virus in clade 2 of the H5 subtype, that can neutralize a H5N1 strain of influenza A virus and have a lambda light chain, and that are IgG antibodies (but not with a IgG1 heavy chain) that can neutralize a H5N1 strain of influenza A virus.

20 Claims, 4 Drawing Sheets

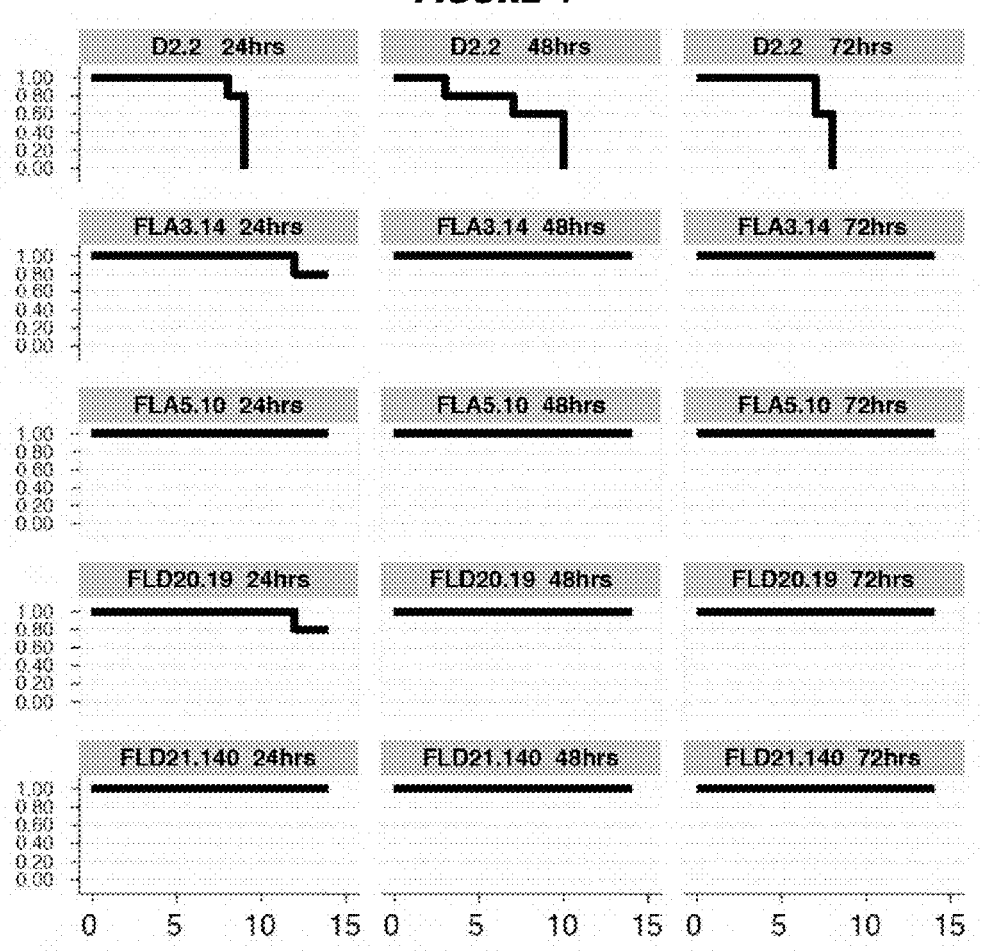

ANTIBODIES AGAINST H5N1 STRAINS OF INFLUENZA A VIRUS

This application claims the benefit of U.S. provisional application No. 60/894,612, filed Mar. 13, 2007, the complete contents of which are incorporated herein by reference.

TECHNICAL FIELD

This invention relates to human antibodies having specificity for influenza virus, and in particular for human H5N1 influenza A virus.

BACKGROUND ART

Influenza A virus is a pathogen that causes serious illness in humans. Strains can be classified by reference to the subtype of their hemagglutinin (HA) and neuraminidase (NA) surface proteins. There are currently sixteen known HA subtypes (H1 to H16), which are antigenically distinct from each other, and nine NA subtypes (N1 to N9). Influenza A viruses currently in circulation in the human population are either H1N1 or H3N2 strains.

Influenza pandemics arise when an influenza A virus strain emerges which is capable of human-to-human (horizontal) transmission and which has a new HA or NA subtype relative to currently circulating strains. For instance, the human population is currently immunologically naïve to H5N1 strains, which have been circulating for some years in avian populations. If a H5N1 strain becomes adapted to human-to-human transmission then it could cause a widespread outbreak of influenza infection.

Current approaches to dealing with an H5N1 outbreak include prophylactic immunization or the use of neuraminidase inhibitors such as oseltamivir (Tamiflu™) and zanamivir (Relenza™). Reference 1 reports that chimeric monoclonal antibodies, with human constant domains (κ light chain and IgG1 heavy chain) and murine variable domains, can neutralize H5N1 viral strains and are thus suitable for use in prophylaxis and therapy. Reference 2 discloses murine monoclonal antibodies prepared against avian influenza strain A/Ck/HK/Yu22/02 and proposes that they might be humanised.

Within the H5 subtype, viruses fall into different lineages, termed clades on the basis of the HA sequence. Viruses isolated in Vietnam and Indonesia in 2004 and 2005, respectively, were designated as reference strains for Clades 1 and 2 (sometimes referred to using roman numerals I and II). The antibodies of reference 1 were prepared against A/Vietnam/1203/04 and A/Hong Kong/213/03 strains, both of which are in clade 1 [3].

There is a need for further and improved materials for preventing and treating H5N1 influenza A virus infections and disease, including the various clades of H5N1.

DISCLOSURE OF THE INVENTION

As explained in more detail below, the inventor has provided human monoclonal antibodies that can neutralize the hemagglutinin of a H5N1 strain of influenza A virus.

The inventor also provides antibodies having one or more CDRs of an antibody selected from the group consisting of FLA5.10, FLD21.140, FLA3.14 and FLD20.19. Preferably these antibodies can neutralize the hemagglutinin of a H5N1 strain of influenza A virus.

The inventor also provides antibodies having one or more CDRs of an antibody selected from the group consisting of FLD84, FLD93, FLD122, FLD127, FLD129, FLD132 and FLD194. Preferably these antibodies can neutralize the hemagglutinin of a H5N1 strain of influenza A virus.

The inventor also provides antibodies that bind to the same epitope as an antibody selected from the group consisting of FLA5.10, FLD21.140, FLA3.14 and FLD20.19. Preferably these antibodies can neutralize the hemagglutinin of a H5N1 strain of influenza A virus.

The inventor also provides antibodies that bind to the same epitope as an antibody selected from the group consisting of FLD84, FLD93, FLD122, FLD127, FLD129, FLD132 and FLD194. Preferably these antibodies can neutralize the hemagglutinin of a H5N1 strain of influenza A virus.

The inventor also provides antibodies that compete for binding to a H5 hemagglutinin protein with an antibody selected from the group consisting of FLA5.10, FLD21.140, FLA3.14, FLD20.19, FLD84, FLD93, FLD122, FLD127, FLD129, FLD132 and FLD194. Preferably these antibodies can neutralize the hemagglutinin of a H5N1 strain of influenza A virus.

The inventor also provides antibodies that can neutralize the hemagglutinin of a strain of influenza A virus in clade 2 of the H5 subtype.

The inventor also provides antibodies that can neutralize the hemagglutinin of a H5N1 strain of influenza A virus, wherein the antibody has a lambda (λ) light chain.

The inventor also provides IgG antibodies that can neutralize the hemagglutinin of a H5N1 strain of influenza A virus, provided that the antibody does not have a IgG1 heavy chain.

The inventor also provides a combination of a first antibody of the invention and a second antibody of the invention, where the first and second antibodies bind to different epitopes on the hemagglutinin of a H5N1 strain of influenza A virus. Thus the antibodies may be able to bind to a single hemagglutinin protein molecule simultaneously. One such combination comprises antibodies FLD20.19 and FLD194. Another combination comprises (i) an antibody that competes for binding to a H5 hemagglutinin protein with FLD20.19 and (ii) an antibody that competes for binding to a H5 hemagglutinin protein with FLD194. Another combination comprises (i) an antibody that binds to the same epitope as FLD20.19 and (ii) an antibody that binds to the same epitope as FLD194.

These various antibodies can be produced in various ways and can be used for preventing and treating viral infections and disease. They can also be used in diagnostic settings.

Human Monoclonal Antibodies

In some embodiments, the invention provides human monoclonal antibodies that can neutralize the hemagglutinin of a H5N1 strain of influenza A virus. Unlike non-human antibodies, these human antibodies will not elicit an immune response directed against their constant domains when administered to humans. Unlike chimeric antibodies, such as those disclosed in reference 1, the variable domains of these human antibodies are 100% human (in particular the framework regions of the variable domains are 100% human, in addition to the complementarity determining regions [CDRs]) and so will not elicit an immune response directed against the variable domain framework regions when administered to humans (except, optionally, for any anti-idiotypic response). The human antibodies do not include any sequences that do not have a human origin.

The term "monoclonal" as originally used in relation to antibodies referred to antibodies produced by a single clonal line of immune cells, as opposed to "polyclonal" antibodies that, while all recognizing the same target protein, were produced by different B cells and would be directed to different epitopes on that protein. As used herein, the word "monoclonal" does not imply any particular cellular origin, but refers to any population of antibodies that all have the same amino acid sequence and recognize the same epitope in the same target protein. Thus a monoclonal antibody may be produced using any suitable protein synthesis system, including immune cells, non-immune cells, acellular systems, etc. This usage is usual in the field e.g. the product datasheets for the CDR-grafted humanised antibody Synagis™ expressed in a murine myeloma NS0 cell line, the humanised antibody Herceptin™ expressed in a CHO cell line, and the phage-displayed antibody Humira™ expressed in a CHO cell line all refer the products as monoclonal antibodies.

Human monoclonal antibodies can be prepared by various means. For example, human B cells producing an antigen of interest can be immortalized e.g. by infection with Epstein Barr Virus (EBV). Human monoclonal antibodies can also be produced in non-human hosts by replacing the host's own immune system with a functioning human immune system e.g. into Scid mice or Trimera mice. Mice transgenic for human Ig loci have been successfully used for generating human monoclonal antibodies (including human antibodies against influenza virus M2 protein [4]) e.g. the "xeno-mouse" from Abgenix [5]. Phage display has also been successful [6], and led to the Humira™ product. A preferred method for producing human monoclonal antibodies is disclosed in references 7 & 8. In this method, a human B memory lymphocyte specific for a target antigen is transformed using EBV in the presence of a polyclonal B cell activator.

In specific embodiments of the invention, the inventor has prepared human monoclonal antibodies referred to herein as FLA5.10, FLD21.140, FLA3.14 and FLD20.19. In further specific embodiments of the invention, the inventor has prepared human monoclonal antibodies referred to herein as FLD84, FLD93, FLD122, FLD127, FLD129, FLD132 and FLD194. These antibodies were prepared using the technique of references 7 & 8.

Antibody FLA5.10 specifically recognizes H5N1 viruses in clade 1. Epitope mapping studies show that it recognizes the HA protein. The amino acid sequence of the variable domain of its heavy chain is SEQ ID NO: 13 (encoded by SEQ ID NO: 14), and the variable domain of its light chain (kappa) is SEQ ID NO: 15 (encoded by SEQ ID NO: 16). Thus its CDRs have the following sequences:

|  | CDR | | | | | |
|---|---|---|---|---|---|---|
|  | H1 | H2 | H3 | L1 | L2 | L3 |
| SEQ ID NO: | 17 | 18 | 19 | 20 | 21 | 22 |

Antibody FLD21.140 specifically recognizes H5N1 viruses in clade 1. It recognizes the HA protein. The amino acid sequence of the variable domain of its heavy chain is SEQ ID NO: (encoded by SEQ ID NO: 6), and the variable domain of its light chain (lambda) is SEQ ID NO: 7 (encoded by SEQ ID NO: 8). Thus its CDRs have the following sequences:

|  | CDR | | | | | |
|---|---|---|---|---|---|---|
|  | H1 | H2 | H3 | L1 | L2 | L3 |
| SEQ ID NO: | 23 | 24 | 25 | 26 | 27 | 28 |

Antibody FLA3.14 recognizes H5N1 viruses in clades 1 and 2. Epitope mapping studies show that it recognizes the HA protein. The amino acid sequence of the variable domain of its heavy chain is SEQ ID NO: 9 (encoded by SEQ ID NO: 10), and the variable domain of its light chain (kappa) is SEQ ID NO: 11 (encoded by SEQ ID NO: 12). Thus its CDRs have the following sequences:

|  | CDR | | | | | |
|---|---|---|---|---|---|---|
|  | H1 | H2 | H3 | L1 | L2 | L3 |
| SEQ ID NO: | 29 | 30 | 31 | 32 | 33 | 34 |

Antibody FLD20.19 recognizes H5N1 viruses in clades 1 and 2. It recognizes the HA protein. The amino acid sequence of the variable domain of its heavy chain is SEQ ID NO: 1 (encoded by SEQ ID NO: 2), and the variable domain of its light chain (kappa) is SEQ ID NO: 3 (encoded by SEQ ID NO: 4). Thus its CDRs have the following sequences:

|  | CDR | | | | | |
|---|---|---|---|---|---|---|
|  | H1 | H2 | H3 | L1 | L2 | L3 |
| SEQ ID NO: | 35 | 36 | 37 | 38 | 39 | 40 |

Antibody FLD84 recognizes H5N1 viruses in clades 1 and 2. It recognizes the HA protein. The amino acid sequence of the variable domain of its heavy chain is SEQ ID NO: 42 (encoded by SEQ ID NO: 41), and the variable domain of its light chain (kappa) is SEQ ID NO: 44 (encoded by SEQ ID NO: 43). Thus its CDRs have the following sequences:

|  | CDR | | | | | |
|---|---|---|---|---|---|---|
|  | H1 | H2 | H3 | L1 | L2 | L3 |
| SEQ ID NO: | 45 | 46 | 47 | 48 | 49 | 50 |

Antibody FLD93 recognizes H5N1 viruses in clades 1 and 2. It recognizes the HA protein. The amino acid sequence of the variable domain of its heavy chain is SEQ ID NO: 52 (encoded by SEQ ID NO: 51), and the variable domain of its light chain (kappa) is SEQ ID NO: 54 (encoded by SEQ ID NO: 53). Thus its CDRs have the following sequences:

|  | CDR | | | | | |
|---|---|---|---|---|---|---|
|  | H1 | H2 | H3 | L1 | L2 | L3 |
| SEQ ID NO: | 55 | 56 | 57 | 58 | 59 | 60 |

Antibody FLD122 recognizes H5N1 viruses in clades 1 and 2. It recognizes the HA protein. The amino acid sequence of the variable domain of its heavy chain is SEQ ID NO: 62 (encoded by SEQ ID NO: 61), and the variable domain of its light chain (kappa) is SEQ ID NO: 64 (encoded by SEQ ID NO: 63). Thus its CDRs have the following sequences:

| | CDR | | | | | |
|---|---|---|---|---|---|---|
| | H1 | H2 | H3 | L1 | L2 | L3 |
| SEQ ID NO: | 65 | 66 | 67 | 68 | 69 | 70 |

Antibody FLD127 recognizes H5N1 viruses in clade 1. It recognizes the HA protein. The amino acid sequence of the variable domain of its heavy chain is SEQ ID NO: 72 (encoded by SEQ ID NO: 71), and the variable domain of its light chain (kappa) is SEQ ID NO: 74 (encoded by SEQ ID NO: 73). Thus its CDRs have the following sequences:

| | CDR | | | | | |
|---|---|---|---|---|---|---|
| | H1 | H2 | H3 | L1 | L2 | L3 |
| SEQ ID NO: | 75 | 76 | 77 | 78 | 79 | 80 |

Antibody FLD129 recognizes H5N1 viruses in clade 1 and pseudotypes bearing influenza H5 HA from viruses in both clades 1 and 2. It recognizes the HA protein. The amino acid sequence of the variable domain of its heavy chain is SEQ ID NO: 82 (encoded by SEQ ID NO: 81), and the variable domain of its light chain (lambda) is SEQ ID NO: 84 (encoded by SEQ ID NO: 83). Thus its CDRs have the following sequences:

| | CDR | | | | | |
|---|---|---|---|---|---|---|
| | H1 | H2 | H3 | L1 | L2 | L3 |
| SEQ ID NO: | 85 | 86 | 87 | 88 | 89 | 90 |

Antibody FLD132 recognizes H5N1 viruses in clade 1 and pseudotypes bearing influenza H5 HA from viruses in both clades 1 and 2. It recognizes the HA protein. The amino acid sequence of the variable domain of its heavy chain is SEQ ID NO: 92 (encoded by SEQ ID NO: 91), and the variable domain of its light chain (kappa) is SEQ ID NO: 94 (encoded by SEQ ID NO: 93). Thus its CDRs have the following sequences:

| | CDR | | | | | |
|---|---|---|---|---|---|---|
| | H1 | H2 | H3 | L1 | L2 | L3 |
| SEQ ID NO: | 95 | 96 | 97 | 98 | 99 | 100 |

Antibody FLD194 recognizes H5N1 viruses in clades 1 and 2. It recognizes the HA protein. The amino acid sequence of the variable domain of its heavy chain is SEQ ID NO: 102 (encoded by SEQ ID NO: 101), and the variable domain of its light chain (kappa) is SEQ ID NO: 104 (encoded by SEQ ID NO: 103). Thus its CDRs have the following sequences:

| | CDR | | | | | |
|---|---|---|---|---|---|---|
| | H1 | H2 | H3 | L1 | L2 | L3 |
| SEQ ID NO: | 105 | 106 | 107 | 108 | 109 | 110 |

The CDR sequences from one or more of these antibodies can be transferred into alternative variable domains in order to create further antibodies sharing their antigen-binding specificity, in the process known as 'CDR grafting' [9-14]. Although the CDR grafting process has typically been used to transfer antigen-binding specificity between variable domains from different animal species, it can also be used to transfer the binding specificity from one type of antibody into a different type of antibody. The H1, H2 and H3 CDRs may be transferred together into an acceptor $V_H$ domain, but it may also be adequate to transfer only one or two of them [12]. Similarly, one two or all three of the L1, L2 and L3 CDRs may be transferred into an acceptor $V_L$ domain. Preferred antibodies will have 1, 2, 3, 4, 5 or all 6 of the donor CDRs. Where only one CDR is transferred, it will typically not be the L2 CDR, which is usually the shortest of the six. Typically the donor CDRs will all be from the same human antibody, but it is also possible to mix them e.g. to transfer the light chain CDRs from a first antibody and the heavy chain CDRs from a second antibody.

The transfer of CDRs from a donor variable domain into an acceptor variable domain is often accompanied by the modification of one or more framework residues.

As an alternative to CDR grafting, the process of 'SDR grafting' may be used [15,16], in which only the specificity-determining residues from within the CDRs are transferred.

By Kabat numbering [17], the CDRs in a light chain variable region are amino acids 24-34 (L1), 50-56 (L2) & 89-97 (L3), and the CDRs in a heavy chain variable region are amino acids 31-35 (H1), 50-65 (H2) and 95-102 (H3). By Chothia numbering [18], the CDRs in a light chain variable region are amino acids 26-32 (L1), 50-52 (L2) & 91-96 (L3), and the CDRs in a heavy chain variable region are amino acids 26-32 (H1), 53-55 (H2) and 96-101 (H3). The tables above define the CDRs by the standardized IMGT numbering system [19-21], namely: CDR1=IMGT positions 27-38; CDR2=IMGT 56-65; and CDR3=IMGT 105-117. Framework or "FR" residues are variable domain residues other than the CDRs.

Reference 22 discloses human monoclonal antibodies against influenza virus, but not against a H5 strain.

Antibodies

Antibodies of the invention can take various forms. For instance, they may be native antibodies, as naturally found in mammals. Native antibodies are made up of heavy chains and light chains. The heavy and light chains are both divided into variable domains and constant domains. The ability of different antibodies to recognize different antigens arises from differences in their variable domains, in both the light and heavy chains. Light chains of native antibodies in vertebrate species are either kappa (κ) or lambda (λ), based on the amino acid sequences of their constant domains. The constant domain of a native antibody's heavy chains will be α, δ, ε, γ or μ, giving rise respectively to antibodies of IgA, IgD, IgE, IgG, or IgM class. Classes may be further divided into subclasses or isotypes e.g. IgG1, IgG2, IgG3, IgG4, IgA, IgA2, etc. Antibodies may also be classified by allotype e.g. a γ heavy chain may have G1m allotype a, f, x or z, G2m allotype n, or G3m allotype b0, b1, b3, b4, b5, c3, c5, g1, g5, s, t, u, or v; a κ light chain may have a Km(1), Km(2) or Km(3) allotype. A native IgG antibody has two identical light chains (one constant domain $C_L$ and one variable domain $V_L$) and two identical heavy chains (three constant domains $C_H1$ $C_H2$ & $C_H3$ and one variable domain $V_H$), held together by disulfide bridges. The domain and three-dimensional structures of the different classes of native antibodies are well known.

Where an antibody of the invention has a light chain with a constant domain, it may be a κ or λ light chain (although, in some embodiments, antibodies must have a λ light chain). Where an antibody of the invention has a heavy chain with a constant domain, it may be a α, δ, ε, γ or μ heavy chain. Heavy chains in the γ class (i.e. IgG antibodies) are preferred. The IgG1 subclass is preferred (although, in some embodiments, antibodies do not have a IgG1 heavy chain). The Synagis™ antibody is IgG1 with a κ light chain. Antibodies of the invention may have any suitable allotype (see above).

Antibodies of the invention may be fragments of native antibodies that retain antigen binding activity. For instance, papain digestion of native antibodies produces two identical antigen-binding fragments, called "Fab" fragments, each with a single antigen-binding site, and a residual "Fc" fragment without antigen-binding activity. Pepsin treatment yields a "F(ab')$_2$" fragment that has two antigen-binding sites. "Fv" is the minimum fragment of a native antibody that contains a complete antigen-binding site, consisting of a dimer of one heavy chain and one light chain variable domain. Thus an antibody of the invention may be Fab, Fab', F(ab')$_2$, Fv, or any other type, of fragment of a native antibody.

An antibody of the invention may be a "single-chain Fv" ("scFv" or "sFv"), comprising a $V_H$ and $V_L$ domain as a single polypeptide chain [23-25]. Typically the $V_H$ and $V_L$ domains are joined by a short polypeptide linker (e.g. ≧12 amino acids) between the $V_H$ and $V_L$ domains that enables the scFv to form the desired structure for antigen binding. A typical way of expressing scFv proteins, at least for initial selection, is in the context of a phage display library or other combinatorial library [26-28]. Multiple scFvs can be linked in a single polypeptide chain [29].

An antibody of the invention may be a "diabody" or "triabody" etc. [30-33], comprising multiple linked Fv (scFv) fragments. By using a linker between the $V_H$ and $V_L$ domains that is too short to allow them to pair with each other (e.g. <12 amino acids), they are forced instead to pair with the complementary domains of another Fv fragment and thus create two antigen-binding sites.

An antibody of the invention may be a single variable domain or VHH antibody. Antibodies naturally found in camelids (e.g. camels and llamas) and in sharks contain a heavy chain but no light chain. Thus antigen recognition is determined by a single variable domain, unlike a mammalian native antibody [34-36]. The constant domain of such antibodies can be omitted while retaining antigen-binding activity. One way of expressing single variable domain antibodies, at least for initial selection, is in the context of a phage display library or other combinatorial library [37]. Reference 38 discloses a camelid antibody (CC07) raised against a H5N2 strain of influenza A virus and having specificity for neuraminidase.

An antibody of the invention may be a "domain antibody" (dAb). Such dAbs are based on the variable domains of either a heavy or light chain of a human antibody and have a molecular weight of approximately 13 kDa (less than one-tenth the size of a full antibody). By pairing heavy and light chain dAbs that recognize different targets, antibodies with dual specificity can be made, and a dAbs of the invention will include at least one domain that can bind to the hemagglutinin of a H5N1 strain of influenza A virus. dAbs are cleared from the body quickly, but can be sustained in circulation by fusion to a second dAb that binds to a blood protein (e.g. to serum albumin), by conjugation to polymers (e.g. to a polyethylene glycol), or by other techniques.

An antibody of the invention may be a chimeric antibody, having constant domains from one organism (e.g. a human) but variable domains from a different organism (e.g. non-human). Chimerisation of antibodies was originally developed in order to facilitate the transfer of antigen specificity from easily-obtained murine monoclonal antibodies into a human antibody, thus avoiding the difficulties of directly generating human monoclonal antibodies. Because the inventor already provided human antibodies as a starting point for further work then chimerisation will not typically be required for performing the invention. If non-human antibodies are generated against a H5N1 strain of influenza A virus, however, then they can be used to prepare chimeric antibodies. Similarly, if human antibodies of the invention are to be used in non-human organisms then their variable domains could be joined to constant domains from the non-human organism.

An antibody of the invention may be a CDR-grafted antibody. The CDR grafting process is described above. Because the inventor already provided human antibodies as a starting point for further work then, as for chimerisation, CDR grafting will not typically be required.

Thus the term "antibody" as used herein encompasses a range of proteins having diverse structural features (usually including at least one immunoglobulin domain having an all-β protein fold with a 2-layer sandwich of anti-parallel β-strands arranged in two β-sheets), but all of the proteins possess the ability to bind to proteins (typically hemagglutinin, which is one of the two main surface glycoproteins) present in the virions of H5N1 strains of influenza A virus.

Antibodies of the invention may include a single antigen-binding site (e.g. as in a Fab fragment or a scFv) or multiple antigen-binding sites (e.g. as in a F(ab')$_2$ fragment or a diabody or a native antibody). Where an antibody has more than one antigen-binding site then advantageously it can result in cross-linking of antigens.

Where an antibody has more than one antigen-binding site, the antibody may be mono-specific (i.e. all antigen-binding sites recognize the same antigen) or it may be multi-specific (i.e. the antigen-binding sites recognise more than one antigen). Thus, in a multi-specific antibody, at least one antigen-binding site will recognise a H5N1 influenza A virus and at least one antigen-binding site will recognise a different antigen.

An antibody of the invention may include a non-protein substance e.g. via covalent conjugation. For example, an antibody may include a radio-isotope e.g. the Zevalin™ and Bexxar™ products include $^{90}Y$ and $^{131}I$ isotopes, respectively. As a further example, an antibody may include a cytotoxic molecule e.g. Mylotarg™ is linked to N-acetyl-γ-calicheamicin, a bacterial toxin. As a further example, an antibody may include a covalently-attached polymer e.g. attachment of polyoxyethylated polyols or polyethylene glycol (PEG) has been reported to increase the circulating half-life of antibodies.

In some embodiments of the invention, an antibody can include one or more constant domains (e.g. including $C_H$ or $C_L$ domains). As mentioned above, the constant domains may form a κ or λ light chain or an α, δ, ε, γ or μ heavy chain. Where an antibody of the invention includes a constant domain, it may be a native constant domain or a modified constant domain. A heavy chain may include either three (as in α, γ, δ classes) or four (as in μ, ε classes) constant domains.

Constant domains are not involved directly in the binding interaction between an antibody and an antigen, but they can provide various effector functions, including but not limited to: participation of the antibody in antibody-dependent cellular cytotoxicity (ADCC); C1q binding; complement dependent cytotoxicity; Fc receptor binding; phagocytosis; and down-regulation of cell surface receptors.

The constant domains can form a "Fc region", which is the C-terminal region of a native antibody's heavy chain. Where an antibody of the invention includes a Fc region, it may be a native Fc region or a modified Fc region. A Fc region is important for some antibodies' functions e.g. the activity of Herceptin™ is Fc-dependent. Although the boundaries of the Fc region of a native antibody may vary, the human IgG heavy chain Fc region is usually defined to stretch from an amino acid residue at position Cys226 or Pro230 to the heavy chain's C-terminus. The Fc region will typically be able to bind one or more Fc receptors, such as a FcγRI (CD64), a FcγRII (e.g. FcγRIIA, FcγRIIB1, FcγRIIB2, FcγRIIC), a FcγRIII (e.g. FcγRIIIA, FcγRIIIB), a FcRn, FcαR (CD89), FcδR, FcμR, a FcεRI (e.g. FcεRIαβγ$_2$ or FcεRIαγ$_2$), FcεRII (e.g. FcεRIIA or FcεRIIB), etc. The Fc region may also or alternatively be able to bind to a complement protein, such as C1q. Modifications to an antibody's Fc region can be used to change its effector function(s) e.g. to increase or decrease receptor binding affinity. For instance, reference 39 reports that effector functions may be modified by mutating Fc region residues 234, 235, 236, 237, 297, 318, 320 and/or 322. Similarly, reference 40 reports that effector functions of a human IgG1 can be improved by mutating Fc region residues (EU Index Kabat numbering) 238, 239, 248, 249, 252, 254, 255, 256, 258, 265, 267, 268, 269, 270, 272, 276, 278, 280, 283, 285, 286, 289, 290, 292, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 and/or 439. Modification of Fc residues 322, 329 and/or 331 is reported in reference 41 for modifying C1q affinity of human IgG antibodies, and residues 270, 322, 326, 327, 329, 331, 333 and/or 334 are selected for modification in reference 42. Mapping of residues important for human IgG binding to FcRI, FcRII, FcRIII, and FcRn receptors is reported in reference 43, together with the design of variants with improved FcR-binding properties. Whole $C_H$ domains can be substituted between isotypes e.g. reference 44 discloses antibodies in which the $C_H3$ domain (and optionally the $C_H2$ domain) of human IgG4 is substituted by the $C_H3$ domain of human IgG1 to provide suppressed aggregate formation. Reference 44 also reports that mutation of arginine at position 409 (EU index Kabat) of human IgG4 to e.g. lysine shows suppressed aggregate formation. Mutation of the Fc region of available monoclonal antibodies to vary their effector functions is known e.g. reference 45 reports mutation studies for RITUXAN™ to change C1q-binding, and reference 46 reports mutation studies for NUMAX™ to change FcR-binding, with mutation of residues 252, 254 and 256 giving a 10-fold increase in FcRn-binding without affecting antigen-binding.

Antibodies of the invention will typically be glycosylated. N-linked glycans attached to the $C_H2$ domain of a heavy chain, for instance, can influence C1q and FcR binding [43], with aglycosylated antibodies having lower affinity for these receptors. The glycan structure can also affect activity e.g. differences in complement-mediated cell death may be seen depending on the number of galactose sugars (0, 1 or 2) at the terminus of a glycan's biantennary chain. An antibody's glycans preferably do not lead to a human immunogenic response after administration.

Antibodies of the invention can be prepared in a form free from products with which they would naturally be associated. Contaminant components of an antibody's natural environment include materials such as enzymes, hormones, or other host cell proteins.

Antibodies of the invention can be used directly (e.g. as the active ingredient for pharmaceuticals or diagnostic reagents), or they can be used as the basis for further development work. For instance, an antibody may be subjected to sequence alterations or chemical modifications in order to improve a desired characteristic e.g. binding affinity or avidity, pharmacokinetic properties (such as in vivo half-life), etc. Techniques for modifying antibodies in this way are known in the art. For instance, an antibody may be subjected to "affinity maturation", in which one or more residues (usually in a CDR) is mutated to improve its affinity for a target antigen. Random or directed mutagenesis can be used, but reference 47 describes affinity maturation by $V_H$ and $V_L$ domain shuffling as an alternative to random point mutation. Reference 48 reports how NUMAX™ was derived by a process of in vitro affinity maturation of the CDRs of the heavy and light chains of SYNAGIS™, giving an antibody with enhanced potency and 70-fold greater binding affinity for RSV F protein.

Preferred antibodies of the invention are specific for antigen from a H5N1 strain of influenza A virus. Thus the antibody will have a tighter binding affinity for that antigen than for an arbitrary control antigen e.g. than for a human protein. Preferred antibodies have nanomolar or picomolar affinity constants for target antigens e.g. $10^{-9}$ M, $10^{-10}$ M, $10^{-11}$ M, $10^{-12}$ M, $10^{-13}$ M or tighter). Such affinities can be determined using conventional analytical techniques e.g. using surface plasmon resonance techniques as embodied in BIAcore™ instrumentation and operated according to the manufacturer's instructions. Radio-immunoassay using radiolabeled target antigen (hemagglutinin) is another method by which binding affinity may be measured.

Antibodies of the invention can recognize clades 1 and/or 2 of H5 viruses. They may also recognize other H5 clades. In some embodiments, antibodies must recognize clade 2. Reference 49 discloses monoclonal antibodies that react with H5 hemagglutinin for use in an immunoassay device.

Neutralizing Activity

Antibodies of the invention can be used to neutralize the hemagglutinin of a H5N1 strain of influenza A virus that can infect human beings. Thus they can neutralize the ability of the virus to initiate and/or perpetuate an infection in a human host. Various assays can be used to determine neutralizing activity, such as the microneutralization assay described herein. Preferred antibodies can neutralize the infectivity of 100 TCID$_{50}$ (50% Tissue Culture Infective Dose) of a H5N1 virus for MDCK cells. H5N1 viruses for use in such assays can be obtained from any suitable source, such as the influenza virus division of the CDC (Atlanta, Ga.). They may also be isolated from infected patients, or by using reverse genetics techniques to combine a H5-subtype HA and a N1-subtype NA with the six other viral segments. As an alternative to using viruses for influenza neutralisation assays, in some embodiments of the invention retroviral pseudotypes bearing influenza H5 HA can be used instead [50].

MDCK cells for use in assays are available from the ATCC under catalog number CCL-34.

In preferred embodiments of the invention, an antibody can neutralise 100 TCID$_{50}$ of a H5N1 influenza A virus at a concentration of 100 μg/ml or lower e.g. 75 μg/ml, 50 μg/ml, 25 μg/ml, 10 μg/ml, 1 μg/ml, 500 ng/ml, 250 ng/ml, 100 ng/ml, 75 ng/ml, 50 ng/ml, 10 ng/ml, or lower. Particularly preferred antibodies can neutralise at 100 ng/ml or lower.

Particularly useful antibodies can, at these concentrations, neutralise 100 TCID$_{50}$ of both a H5N1 influenza A virus strain in clade 1 and a H5N1 influenza A virus strain in clade 2.

The ability to neutralize a H5 strain of influenza A virus does not necessarily mean that the antibodies cannot neutralize any of the other 15 hemagglutinin subtypes. In some embodiments antibodies may neutralize multiple hemagglutinin subtypes (e.g. all 16 subtypes). In other embodiments, antibodies may not neutralize a H3N2 influenza virus. In other embodiments, antibodies may neutralize only H5 subtypes.

Nucleic Acids and Recombinant Antibody Expression

The invention also encompasses nucleic acid sequences encoding antibodies of the invention. Where an antibody of the invention has more than one chain (e.g. a heavy chain and a light chain), the invention encompasses nucleic acids encoding each chain. The invention also encompasses nucleic acid sequences encoding the amino acid sequences of CDRs of antibodies of the invention.

Nucleic acids encoding the antibodies can be prepared from cells, viruses or phages that express an antibody of interest. For instance, nucleic acid (e.g. mRNA transcripts, or DNA) can be prepared from an immortalised B cell of interest, and the gene(s) encoding the antibody of interest can then be cloned and used for subsequent recombinant expression. Expression from recombinant sources is more common for pharmaceutical purposes than expression from B cells or hybridomas e.g. for reasons of stability, reproducibility, culture ease, etc. Methods for obtaining and sequencing immunoglobulin genes from B cells are well known in the art e.g. see reference 51. Thus various steps of culturing, sub-culturing, cloning, sub-cloning, sequencing, nucleic acid preparation, etc. can be performed in order to perpetuate the antibody expressed by a cell or phage of interest. The invention encompasses all cells, nucleic acids, vectors, sequences, antibodies etc. used and prepared during such steps.

The invention provides a method for preparing one or more nucleic acid molecules (e.g. heavy and light chain genes) that encodes an antibody of interest, comprising the steps of: (i) providing an immortalised B cell clone expressing an antibody of interest; (ii) obtaining from the B cell clone nucleic acid that encodes the antibody of interest. The nucleic acid obtained in step (ii) may be inserted into a different cell type, or it may be sequenced.

The invention also provides a method for preparing a recombinant cell, comprising the steps of: (i) obtaining one or more nucleic acids (e.g. heavy and/or light chain genes) from a B cell clone that encodes an antibody of interest; and (ii) inserting the nucleic acid into an expression host in order to permit expression of the antibody of interest in that host.

Similarly, the invention provides a method for preparing a recombinant cell, comprising the steps of: (i) sequencing nucleic acid(s) from a B cell clone that encodes the antibody of interest; and (ii) using the sequence information from step (i) to prepare nucleic acid(s) for inserting into an expression host in order to permit expression of the antibody of interest in that host.

Recombinant cells produced in these ways can then be used for expression and culture purposes. They are particularly useful for expression of antibodies for large-scale pharmaceutical production.

The invention provides a method for preparing an antibody of the invention, comprising a step of culturing a cell such that it produces the antibody. The methods may further comprise a step of recovering the antibody that has been produced, to provide a purified antibody. A cell used in these methods may, as described elsewhere herein, be a recombinant cell, an immortalised B cell, or any other suitable cell. Purified antibody from these methods can then be used in pharmaceutical and/or diagnostic compositions, etc.

Cells for recombinant expression include bacteria, yeast and animal cells, particularly mammalian cells (e.g. CHO cells, human cells such as PER.C6 (ECACC deposit 96022940 [52]), NSO cells (ECACC deposit 85110503) or HKB-11 [53,54] cells), etc.), as well as plant cells. Preferred expression hosts can glycosylate the antibody of the invention, particularly with carbohydrate structures that are not themselves immunogenic in humans (see above). Expression hosts that can grow in serum-free media are preferred. Expression hosts that can grow in culture without the presence of animal-derived products are preferred.

The expression host may be cultured to give a cell line.

Nucleic acids used with the invention may be manipulated to insert, delete or amend certain nucleic acid sequences. Changes from such manipulation include, but are not limited to, changes to introduce restriction sites, to amend codon usage, to add or optimise transcription and/or translation regulatory sequences, etc. It is also possible to change the nucleic acid to alter the encoded amino acids. For example, it may be useful to introduce one or more (e.g. 1, 2, 3, 4, 5, 6, 7, 8, 9, 10, etc.) amino acid substitutions, one or more (e.g. 1, 2, 3, 4, 5, 6, 7, 8, 9, 10, etc.) amino acid deletions, and/or one or more (e.g. 1, 2, 3, 4, 5, 6, 7, 8, 9, 10, etc.) amino acid insertions into the antibody's amino acid sequence. Such point mutations can modify effector functions, antigen-binding affinity, post-translational modifications, immunogenicity, etc., can introduce amino acids for the attachment of covalent groups (e.g. labels) or can introduce tags (e.g. for purification purposes). Mutations can be introduced in specific sites or can be introduced randomly, followed by selection (e.g. molecular evolution).

Particular nucleic acid sequences according to the invention comprise one or more of SEQ ID NOS: 2, 4, 6, 8, 10, 12, 14 and/or 16.

Nucleic acids of the invention may be present in a vector (such as a plasmid) e.g. in a cloning vector or in an expression vector. Thus a sequence encoding an amino acid sequence of interest may be downstream of a promoter such that its transcription is suitable controlled. The invention provides such vectors, and also provides cells containing them.

The invention also provides an immortalised human B cell that can secrete an antibody that can neutralize the hemagglutinin of a H5N1 strain of influenza A virus. The invention also provides an immortalised human B cell that can secrete an antibody of the invention.

Pharmaceutical Compositions

The use of antibodies as the active ingredient of pharmaceuticals is now widespread, including the products Herceptin™ (trastuzumab), Rituxan™, Mylotarg™, Zevalin™ Synagis™ (palivizumab), Zenapax™ (daclizumab), etc. Synagis™ and Numax™ (motavizumab) in particular are effective in preventing respiratory tract disease. The inventor thus provides a pharmaceutical composition containing one or more antibody(ies) of the invention. Techniques for purification of monoclonal antibodies to a pharmaceutical grade are well known in the art.

A combination of at least one antibody that can neutralise a clade 1 strain of H5N1 influenza A virus and at least one antibody that can neutralise a clade 2 strain of H5N1 influenza A virus is particularly useful. A combination comprising two antibodies that bind to different epitopes on the hemagglutinin of a H5N1 strain of influenza A virus is also useful. The antibodies in these combinations may be given to a patient by simultaneous separate or sequential administration.

As an alternative to delivering antibodies to a patient as an active ingredient (e.g. in passive immunisation), it is possible to deliver a peptide including an epitope recognised by an antibody of the invention (e.g. in active immunisation). Thus a pharmaceutical composition of the invention may contain a polypeptide comprising an epitope recognised by an antibody selected from the group consisting of FLA5.10, FLD21.140, FLA3.14, FLD20.19, FLD84, FLD93, FLD122, FLD127, FLD129, FLD132 and FLD194. The polypeptide may be shorter than a full-length HA0, HA1 or HA2 peptide.

As a further alternative to delivering antibodies, it is possible to deliver nucleic acid encoding the antibodies such that the nucleic acid can be expressed in a patient in situ. Thus a pharmaceutical composition of the invention may contain nucleic acid encoding an antibody of the invention. Nucleic acid may be in form of replicating or non-replicating vector. Viral or non-viral vectors may be used. Suitable gene therapy and nucleic acid delivery vectors are known in the art.

A pharmaceutical composition will usually contain one or more pharmaceutically acceptable carriers and/or excipient(s). A thorough discussion of such components is available in reference 55. These may include liquids such as water, saline, glycerol and ethanol. Additionally, auxiliary substances, such as wetting or emulsifying agents or pH buffering substances, may be present in such compositions.

Pharmaceutical compositions may be prepared in various forms e.g. as injectables, either as liquid solutions or suspensions. Solid forms suitable for solution in, or suspension in, liquid vehicles prior to injection can also be prepared (e.g. a lyophilised composition, like Synagis™ and Herceptin™, for reconstitution with sterile water or buffer, optionally containing a preservative). The composition may be prepared for topical administration e.g. as an ointment, cream or powder. The composition may be prepared for oral administration e.g. as a tablet or capsule, as a spray, or as a syrup (optionally flavoured), in which case it will usually contain agents to protect the active ingredients from degradation. The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted (e.g. with sterile water or a sterile buffer) at the time of use, prior to administration to a patient e.g. an antibody can be provided in dry form.

Preferred pharmaceutical forms for administration of antibodies include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain carriers/excipients such as suspending, preservative, stabilising and/or dispersing agents.

Pharmaceutical compositions will generally have a pH between 5.5 and 8.5, preferably between 6 and 8, and more preferably about 7. The pH may be maintained by a buffer.

The composition will usually be sterile. The composition will usually be non-pyrogenic e.g. containing <1 EU (endotoxin unit, a standard measure) per dose, and preferably <0.1 EU per dose. The composition is preferably gluten free. The composition may be substantially isotonic with respect to humans.

Compositions may include an antimicrobial and/or preservative.

Compositions may comprise a detergent. Where present, detergents are generally used at low levels e.g. <0.01%.

Compositions may include sodium salts (e.g. sodium chloride) to give tonicity. A concentration of 10±2 mg/ml NaCl is typical.

Compositions may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material.

Compositions may include free amino acids e.g. histidine. For instance, reference 56 discloses an improved aqueous formulation for the Synagis™ antibody comprising histidine in an aqueous carrier.

Pharmaceutical compositions will include an effective amount of the active ingredient. The concentration of the ingredient in a composition will, of course, vary according to the volume of the composition to be delivered, and known antibody-based pharmaceuticals provide guidance in this respect. For example, Synagis™ is provided for reconstitution to give 50 mg antibody in 0.5 ml or 100 mg of antibody in 1.0 ml. The appropriate volume is delivered to a patient based on their recommended dose.

Once formulated, the compositions of the invention can be administered directly to the subject (see below). It is preferred that the compositions are adapted for administration to human subjects. This will generally be in liquid (e.g. aqueous) form.

In compositions that include antibodies, particularly pharmaceutical compositions, the antibodies preferably make up at least 50% by weight (e.g. at least 60%, 70%, 80%, 90%, 95%, 97%, 98%, 99% or more) of the total protein in the composition. The antibodies are thus in purified form.

Pharmaceutical compositions of the invention are preferably supplied in hermetically-sealed containers.

The invention also provides a method of preparing a pharmaceutical composition, comprising a step of admixing an antibody of the invention with one or more pharmaceutically acceptable ingredients.

Medical Treatments and Uses

Antibodies of the invention may be used for the treatment and/or prevention of disease caused by a H5N1 strain of influenza A virus, particularly in humans. Thus the invention provides an antibody of the invention for use in therapy. Also provided is a method of treating a patient comprising administering to that patient an antibody of the invention. Also provided is the use of an antibody of the invention, in the manufacture of a medicament for the treatment and/or prevention of disease caused by a H5N1 strain of influenza A virus. Also provided is an antibody of the invention for use in the treatment and/or prevention of disease caused by a H5N1 strain of influenza A virus.

The inventor also provides a first antibody and a second antibody for simultaneous separate or sequential administration. In some embodiments the first and second antibodies can between them neutralise a clade 1 strain and a clade 2 strain, as described above. In some embodiments, the first and second antibodies bind to different epitopes on the same H5 hemagglutinin, as described above.

The inventor also provides said first and second antibodies for combined use in therapy. They also provide a combination of said first and second antibodies for use in therapy. They also provide said first and second antibodies for use in a method of treatment and/or prevention of disease caused by a H5N1 strain of influenza A virus.

The inventor also provides the use of said first and second antibodies in the manufacture of a medicament for the treatment and/or prevention of disease caused by a H5N1 strain of influenza A virus. They also provide the use of said first antibody in manufacture of medicament for the treatment and/or prevention of disease caused by a H5N1 strain of influenza A virus, wherein the medicament is prepared for administration with said second antibody. Similarly, they provide the use of said second antibody in manufacture of medicament for the treatment and/or prevention of disease caused by a H5N1 strain of influenza A virus, wherein the medicament is prepared for administration with first second antibody.

The inventor also provides the use of said first antibody in manufacture of medicament for the treatment and/or prevention of disease caused by a H5N1 strain of influenza A virus, wherein the patient has previously been treated with the second antibody. Similarly, they provide the use of said second antibody in manufacture of medicament for the treatment and/or prevention of disease caused by a H5N1 strain of influenza A virus, wherein the patient has previously been treated with the first antibody. The pre-treated patient may still have the previously administered antibody in circulation in the body.

The inventor also provides said first antibody for use in a method of treatment and/or prevention of disease caused by a H5N1 strain of influenza A virus, wherein said first antibody is administered (or is prepared for administration) with said second antibody. They also provide said second antibody for use in a method of treatment and/or prevention of disease caused by a H5N1 strain of influenza A virus, wherein said second antibody is administered (or is prepared for administration) with said first antibody.

The therapeutic uses of the antibodies are relevant both to zoonotic infections of humans with H5N1 viruses from non-human organisms (typically avian) and to human pandemic outbreaks of H5N1 influenza.

Antibodies can be used for immunoprophylaxis (passive immunization) and/or immunotherapy. To confirm prophylactic efficacy without imposing an infectious challenge on a patient, circulating antibody levels can be tested e.g. in a neutralization assay. To confirm therapeutic efficacy after administration of a pharmaceutical composition of the invention, any known methods for assessing the presence and/or severity of influenza A virus infection can be used. Such methods are commonly used for influenza in the antiviral and vaccine fields.

Treatment may be targeted at patient groups that are particularly at risk of or susceptible to H5N1 infection. Such subjects groups include, but are not limited to: immunocompromised subjects, such as those suffering from HIV or undergoing immunosuppressive therapy e.g. transplant patients; the elderly (e.g. $\geq 50$ years old, $\geq 60$ years old, and preferably $\geq 65$ years); the young (e.g. $\leq 5$ years old); hospitalised patients; healthcare workers; armed service and military personnel; pregnant women; the chronically ill; immunodeficient patients; patients who have taken an antiviral compound (e.g. an oseltamivir or zanamivir compound) in the 7 days prior to receiving the vaccine; patients who have been treated with an antiviral compound but have shown an inadequate antiviral response; and people travelling abroad.

Pharmaceutical compositions of the invention may be administered by any number of routes including, but not limited to, intravenous, intramuscular, intra-arterial, intramedullary, intraperitoneal, intrathecal, intraventricular, transdermal, transcutaneous, oral, topical, subcutaneous, intranasal, enteral, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide some guidance relating to frequency of administration e.g. whether a pharmaceutical should be delivered daily, weekly, monthly, etc. Frequency and dosage may also depend on the severity of symptoms.

Patients will receive an effective amount of the active ingredient i.e. an amount that is sufficient to treat, ameliorate, or prevent H5N1 influenza A virus infection. Therapeutic effects may also include reduction in physical symptoms. The optimum effective amount for any particular subject will depend upon their size and health, the nature and extent of the condition, and the therapeutics or combination of therapeutics selected for administration. The effective amount delivered for a given situation can be determined by routine experimentation and is within the judgment of a clinician. For purposes of the present invention, an effective dose will generally be from about 0.01 mg/kg to about 50 mg/kg, or about 0.05 mg/kg to about 10 mg/kg of the compositions of the present invention in the individual to which it is administered. Known antibody-based pharmaceuticals provide guidance in this respect e.g. Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; Synagis™ is administered intramuscularly at 15 mg/kg body weight, typically once a month during the RSV season; etc.

Antibodies of the invention may be administered (either combined or separately) with other therapeutics e.g. with an antiviral compound active against influenza virus (e.g. oseltamivir and/or zanamivir). These antivirals include neuraminidase inhibitors, such as a (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (Tamiflu™). Such combination therapy may provide a synergistic improvement in therapeutic efficacy. Such antivirals are particularly useful when administered in combination therapy with more than one antibody of the invention, as disclosed elsewhere herein.

Diagnosis

As well as being therapeutically useful, the binding activity of antibodies of the invention (including non-neutralising antibodies) means that they can be used in diagnostics. Antibodies may be employed as reagents in immunoassays, radioimmunoassays (RIA), enzyme-linked immunosorbent assays (ELISA), etc. Antibodies of the invention may thus be attached to a solid support. This attachment can facilitate their use in diagnostic assays. It can also facilitate their use in purification of their target antigens.

Antibodies of the invention may be labelled with an analytically-detectable reagent such as a radioisotope, a fluorescent molecule or an enzyme. This labelling facilitates their use in diagnostic assays.

In some embodiments, antibodies of the invention can be used as reagents in immunoassays for screening and/or identifying antigenic or immunogenic peptides e.g. to identify peptides that might elicit a useful anti-HA response when administered to a patient.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Different steps in a method of the invention can optionally be performed at different times by different people in different places (e.g. in different countries).

BRIEF DESCRIPTION OF DRAWINGS

FIG. 4 shows the proportion of mice surviving (%) over a 15 day period after infection (at day 0) in a serotherapy experiment (Kaplan-Meier survival curve) of BALB/c mice intranasally infected 24, 48 or 72 hours previously with 5 LD50 of A/Vietnam/1203/04.

MODES FOR CARRYING OUT THE INVENTION

Generation of Immortalised B Cells

Figure 1:
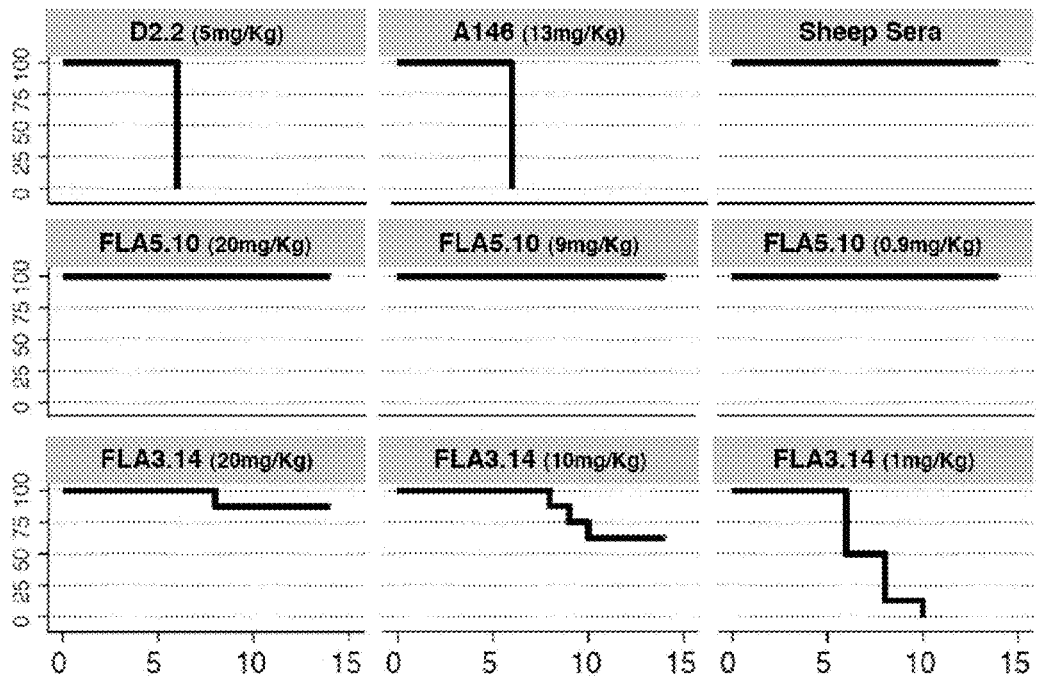
FIG. 1 shows the proportion of mice surviving (%) over a 15 day period after infection (at day 0) in an immunoprophylaxis experiment (Kaplan-Meier survival curve).

Four adults were diagnosed with HPAI (highly pathogenic avian influenza) H5N1 infection. During early convalescence (1-4 months post illness onset), all subjects had detectable neutralizing antibody titers to their autologous virus. After receiving written informed consent from the patients, blood was taken from all four patients.

Frozen peripheral blood mononuclear cells (PBMCs) were thawed and stained with antibodies against CD22, IgM, IgD and IgA. CD22$^+$ IgM$^-$, IgD$^-$, IgA$^-$ B cells were isolated using a FACSAria machine. The B cells were then immortalized at 30 cells/well using EBV in the presence of CpG oligodeoxynucleotide 2006 and irradiated allogeneic PBMC [8]. Cells were cultured in complete RPMI 1640 (cRPMI) supplemented with 10% foetal calf serum. Culture supernatants were harvested after 14 days and screened for neutralizing activity.

Neutralization was assessed by a microneutralization assay using MDCK cells and 100 TCID$_{50}$ of A/VietNam/1203/04 (H5N1), essentially as described in reference 58. Briefly, neat supernatants were incubated with 100 TCID$_{50}$ of virus for 1 hr at room temperature prior to addition to monolayers of MDCK cells. Cell monolayers were incubated for a further 2-3 days and examined for cytopathic effect (CPE). Determination of endpoint neutralising antibody titres was performed in a similar fashion, except that plasma or supernatant samples were serially two-fold diluted prior to mixing with 100 TCID$_{50}$ of virus. Plasma samples were tested at a starting dilution of 1:10, whilst supernatants were tested at a starting dilution of 1:8 and residual infectivity was tested in 4 wells per dilution. Neutralizing titer was defined as the reciprocal of the highest dilution of serum at which the infectivity of 100 TCID$_{50}$ of the appropriate wild-type H5N1 virus for MDCK cells was completely neutralized in 50% of the wells. Infectivity was identified by the presence of CPE on day 4 and the titer was calculated by the Reed-Muench method.

Cultures with measurable neutralizing activity were cloned by limiting dilution at 0.5 cell/well in the presence of CpG 2006 and irradiated PBMCs. B cell clones were cultured at high cell density in cRPMI 10% Ig-depleted FCS in CELLine Two-Compartment Bioreactors to produce enriched supernatants containing 1-3 mg/ml of antibody. Antibodies were also purified on protein G columns. The isotype, subclass and light chain of the antibodies were characterized by ELISA using specific antibodies and HRP-labelled anti-human Ig antibody. Antibodies were quantified with reference to a standard certified preparation (Sigma-Aldrich, Buchs, SG).

Several independent clones producing neutralizing human antibodies were isolated. Clones producing antibodies that recognized H5-HA by ELISA, but did not neutralize live virus, were also identified from each donor. Four clones named 'FLA3.14', 'FLA5.10', 'FLD20.19' and 'FLD21.140' were selected for further study. All clones secreted an IgG1 antibody with neutralising activity against influenza A clade 1 H5N1 viruses isolated in Vietnam. Neutralisation titres with the human antibodies were recorded against 100 TCID$_{50}$ of three different H5N1 clade 1 strains:

| Ab (concentration) | Reciprocal neutralising titre against indicated strain | | |
|---|---|---|---|
| | VN/CL26/04 | VN/115/05 | VN/VL1/06 |
| FLA5.10 (0.7 mg/ml) | 2958 | 107 | 1782 |
| FLA3.14 (1.5 mg/ml) | 372 | 208 | 1260 |
| FLD20.19 (1.5 mg/ml) | 1,280 | 4,012 | 2,460 |
| FLD21.140 (1.5 mg/ml) | 896 | 2,880 | 3,208 |
| D2.2 (0.7 mg/ml) | <10 | <10 | <10 |

NB: D2.2 is a control antibody that does not recognize influenza virus

FLA5.10 and FLD21.140 demonstrated in vitro neutralizing activity against reference strains of clade 1 H5N1 viruses, with FLD21.140 being more potent than FLA5.10. FLA3.14 and FLD20.19 demonstrated in vitro neutralizing activity against reference H5N1 viruses of both clade 1 and clade 2. FLD20.19 in particular was highly effective at neutralizing clades 1 and 2 H5N1 influenza A viruses. None of the antibodies neutralised a H3N2 influenza virus A/California/7/04. Reciprocal neutralising titres were as follows, normalized to an antibody concentration of 1 mg/ml:

|  | Strain | | | | | |
| --- | --- | --- | --- | --- | --- | --- |
|  | HK/491/97 | HK/213/03 | VN/1203/04 | JPHN/30321/05 | Indo/5/05 | CA/7/04 |
| Subtype | H5N1 | H5N1 | H5N1 | H5N1 | H5N1 | H3N2 |
| H5N1 clade | 1 | 1 | 1 | 1 | 2 | — |
| FLA3.14. | 403 | 508 | 226 | 508 | 508 | 10 |
| FLA5.10 | 127 | 4,064 | 508 | 806 | 10 | 10 |
| FLD20.19 | 905 | 5,120 | 1,613 | 6,451 | 5,120 | 10 |
| FLD21.140 | 32 | ≧14,882 | 5,120 | 12,902 | 10 | 19 |
| D2.2 | <10 | <10 | <10 | <10 | <10 | <10 |

Another series of monoclonal antibodies was generated from B cells isolated from frozen PBMCs of one of the 4 donors. Several independent clones producing neutralizing human antibodies were isolated. Seven clones named 'FLD84', 'FLD93', 'FLD122', 'FLD127', 'FLD129', 'FLD132' and 'FLD194' were selected for further study. FLD127, FLD129 and FLD132 demonstrated in vitro neutralizing activity against reference strains of clade 1 H5N1 viruses, with FLD132 and FLD129 being more potent than FLD127. FLD84, FLD93, FLD122, FLD194 demonstrated in vitro neutralizing activity against reference H5N1 viruses of both clade 1 and clade 2. FLD194 and FLD122 in particular were highly effective at neutralizing clades 1 and 2 H5N1 influenza A viruses. Reciprocal neutralising titres of culture supernatants were as follows:

|  | Reciprocal neutralising titre: | | |
| --- | --- | --- | --- |
| Name | HK/491/97 H5N1 clade 1 | VN/1203/04 H5N1 clade 2 | Indo/5/05 H5N1 clade 2 |
| FLD20.19* | 181 | 181 | 813 |
| FLD84 | 40 | 16 | 102 |
| FLD93 | 20 | 40 | 406 |
| FLD122 | 161 | 40 | 362 |
| FLD127 | 102 | 81 | <8 |
| FLD129 | 1448 | 323 | <8 |
| FLD132 | 2048 | 1024 | <8 |
| FLD194 | 406 | 102 | 406 |

*these titers with FLD20.19 cannot be directly compared to the previous data. This assay used a different initial concentration of the antibody and a different dose of virus.

In particular, FLD122 and FLD194 neutralize the three viruses tested with potency comparable to that shown by the best monoclonal antibody isolated in the previous screening (FLD20.19).

Prophylactic and Therapeutic Serotherapy in Mice

BALB/c mice are highly susceptible to infection with the HPAI H5N1 viruses isolated in Asia in 1997 and since 2003. Following intranasal administration, the H5N1 viruses isolated in Asia since 1997 replicate to high titer in the lungs of mice and some isolates disseminate to extrapulmonary sites and are lethal for mice. To explore the efficacy of the anti-H5N1 human antibodies for pre-exposure immunoprophylaxis or post-exposure immunotherapy, BALB/c mice were either passively immunized with the antibodies and then challenged 24 hrs later intranasally with A/Vietnam/1203/04 (H5N1) or challenged with A/Vietnam/1203/04 (H5N1) and 24, 48 or 72 hours later injected with an antibody. Groups of 4-8 female BALB/c mice (4-6 weeks old) were used in all experiments. Inoculation of mice and tissue harvests were performed in a biosafety cabinet by personnel wearing powered air purifying respirators.

To measure prophylactic efficacy, mice were intraperitoneally (i.p.) injected with 1 ml of monoclonal antibody FLA3.14 or FLA5.10 in graded doses, or with hyperimmune sheep antisera raised against recombinant HA of A/VN/1203/2004 (H5N1). As controls, mice received human monoclonal antibody D2.2 (specific for diphtheria toxin) or A146 (specific for anthrax protective antigen). 24 hours after i.p. administration, mice were bled for measurement of neutralizing antibody titres, then intranasally challenged with $10^5$ $TCID_{50}$ of A/Vietnam/1203/04 (H5N1) in 50 µl. Mice were observed and weighed daily before and after viral infection. As shown in FIG. 1, mice that received hyperimmune anti-H5 polyclonal sheep antiserum were afforded complete protection. All preparations of FLA5.10 conferred 100% protection from lethality by A/Vietnam/1203/04 in the prophylactic efficacy assay. FLA3.14 also conferred protection from lethality, but with lower efficacy and in a dose dependent manner. Mice receiving the highest dose of FLA3.14 were afforded almost complete protection. The lowest dose tested for FLA3.14 (1 mg/kg) delayed time to death but did not prevent fatal infection. These data, demonstrating the relatively greater potency of FLA5.10 over FLA3.14 in vivo, are consistent with the in vitro neutralization titres measured against A/Vietnam/1203/04 (see above).

Figure 2:
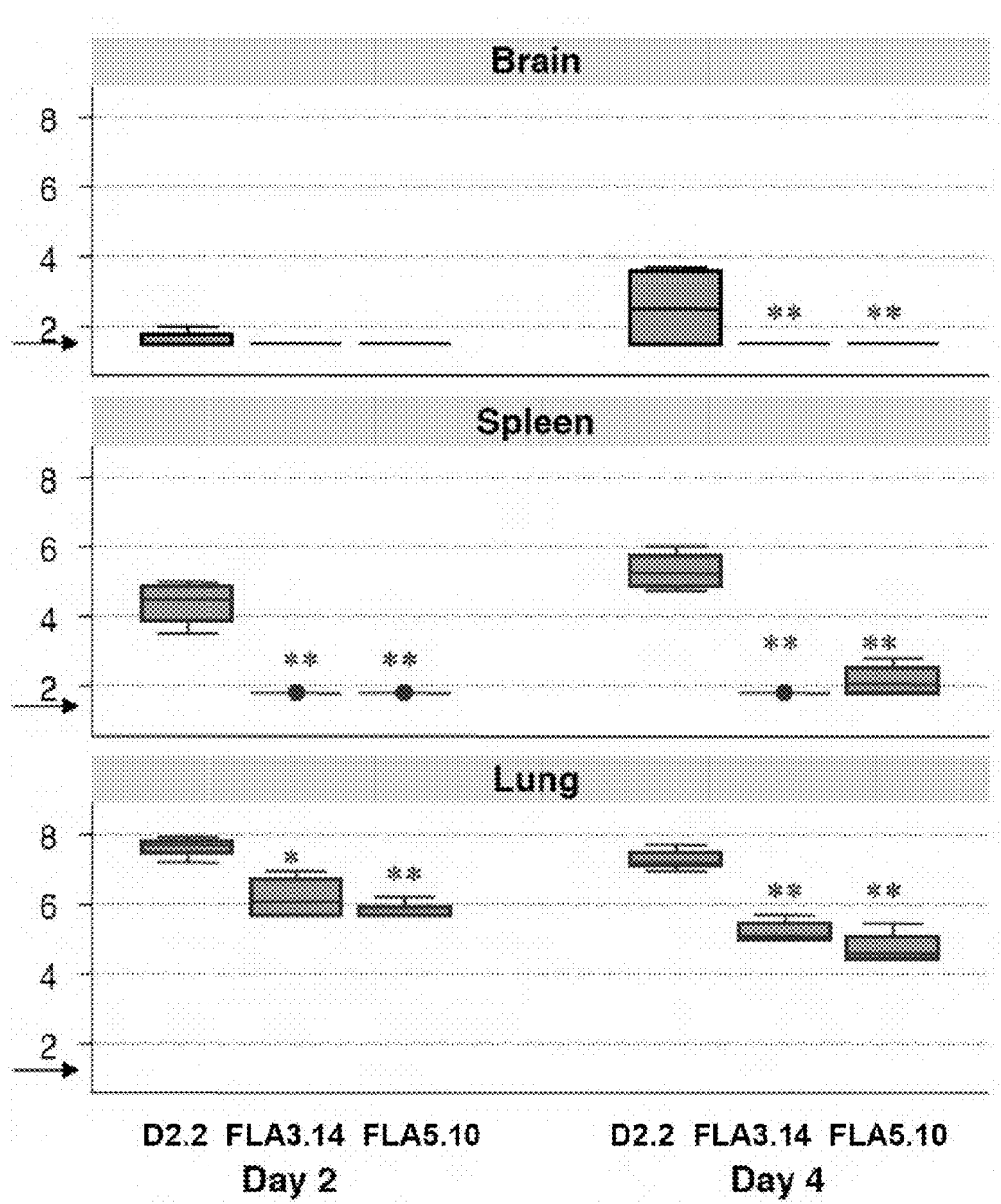
FIG. 2 shows mean viral titres ($\log_{10}$ TCID$_{50}$ per gram of tissue) in brain, spleen and lung of mice in a prophylaxis study. Data for antibodies D2.2 (control), FLA3.14 and FLA5.10 are shown at days 2 and 4 after infection. Asterisks indicate statistical significance (*=P<0.01 versus D2.2; **=P<0.001 versus D2.2). The arrows show the lower limit of detection in the assay (1.5 $\log_{10}$ TCID$_{50}$/g).

To explore how FLA3.14 and FLA5.10 antibodies might confer protection from lethality, the kinetics of viral infection in passively immunized mice were studied. Mice passively immunized with FLA3.14, FLA5.10 or D2.2 were challenged with A/Vietnam/1203/04 (H5N1) 24 hours later. On days 2 and 4 mice were killed and lungs, brains and spleens aseptically removed. Tissues were homogenized in Leibovitz L-15 medium supplemented with antibiotic-antimycotic solution to achieve suspensions of lung (10% w/v), spleen (5% w/v) and brain (10% w/v), which were then titrated on monolayers of MDCK cells in quadruplicate. Viral titres were calculated by the Reed Muench method and expressed as $\log_{10}$ $TCID_{50}$ per g of tissue. FIG. 2 shows that on days 2 and 4 there was significantly less virus recovered in brain, splenic and pulmonary tissue of mice that received either FLA3.14 or FLA5.10 than mice that received the control D2.2 antibody.

Figure 3:
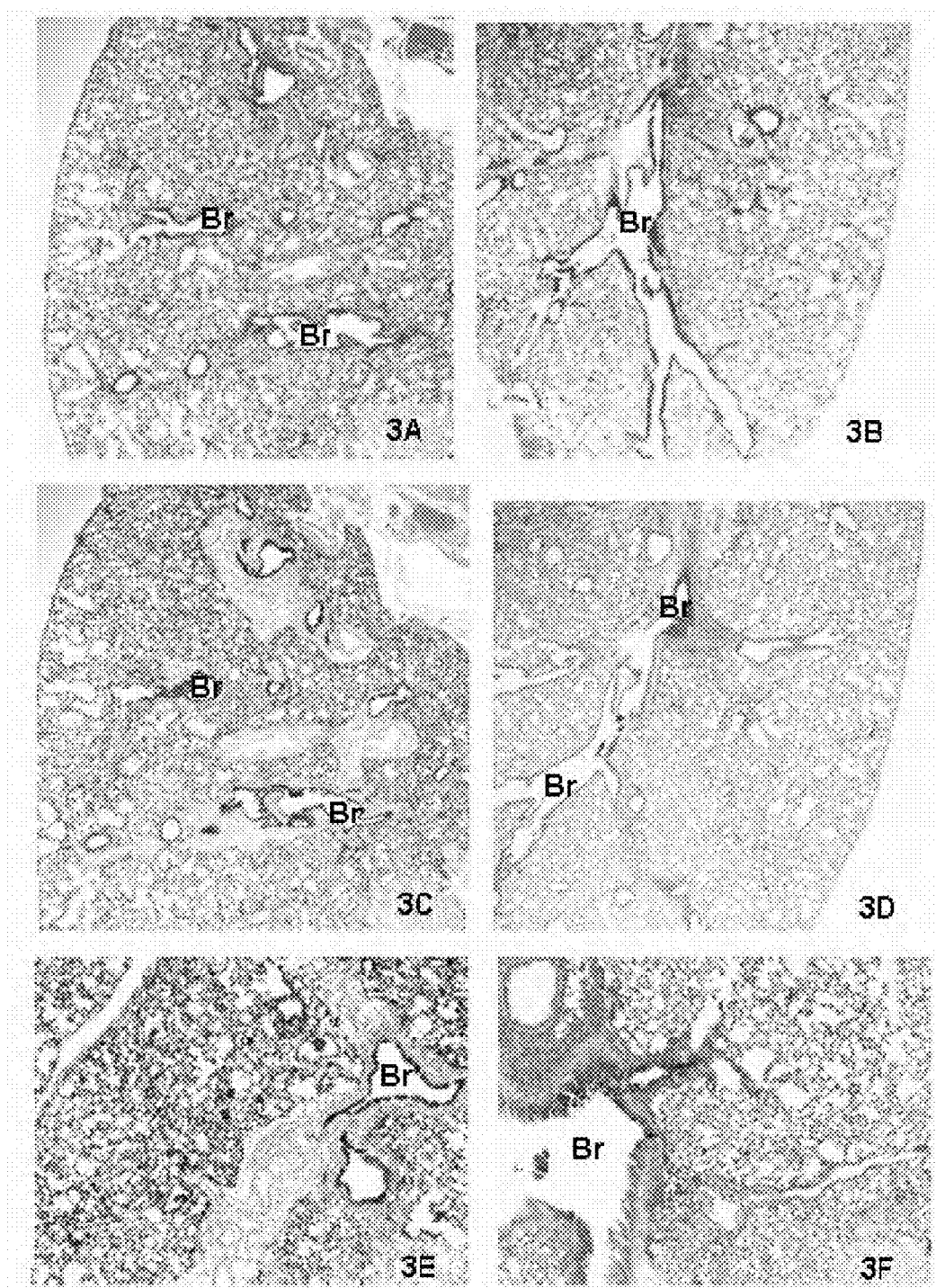
FIG. 3 shows immunohistochemical analysis of lungs from mice. Panels A & C show lungs from mice treated with FLA5.10 antibody. Panels B & D show lungs from untreated control mice. Panels E & F are magnified views of panels B & D. 'Br' indicates a bronchiole.

To perform pathology studies, mice were necropsied and the lungs inflated with 10% neutral buffered formalin, embedded in paraffin and sections prepared. Slides were stained with hematoxylin and eosin. For immunohistochemical demonstration of H5 antigen, paraffin sections were prepared and ABC immunohistochemistry was performed using a goat antibody to avian influenza H5 goat alpha H5 diluted at 1:1000, with a Vector rabbit anti-goat secondary and the Vector ABC Elite label diaminobenzidine as the chromogen and hematoxylin as the counterstain. FIG. 3 shows that mice that received prophylaxis with FLA5.10 had less dramatic pathological changes in pulmonary airways and parenchymal tissue. Thus, the percentage of abnormal bronchioles with necrosis and viral HA antigen in lung sections from mice that received FLA5.10 prophylaxis was less (13%) than in control mice (80%) (FIG. 3, panels A & C vs. B & D or vs. E & F).

Similarly, there were fewer inflammatory interstitial (I) lesions in which H5 antigen was detected by immunohistochemical staining in the lung sections of mice given FLA5.10 relative to the control antibody, D2.2 (1 vs. 10+). These data suggest that prophylaxis with FLA3.14 or FLA5.10 probably confers protection from lethal challenge through a combination of limiting viral replication in the lung, attenuating virus-induced lung pathology and blocking extrapulmonary dissemination of virus to distant organs.

Figure 5:
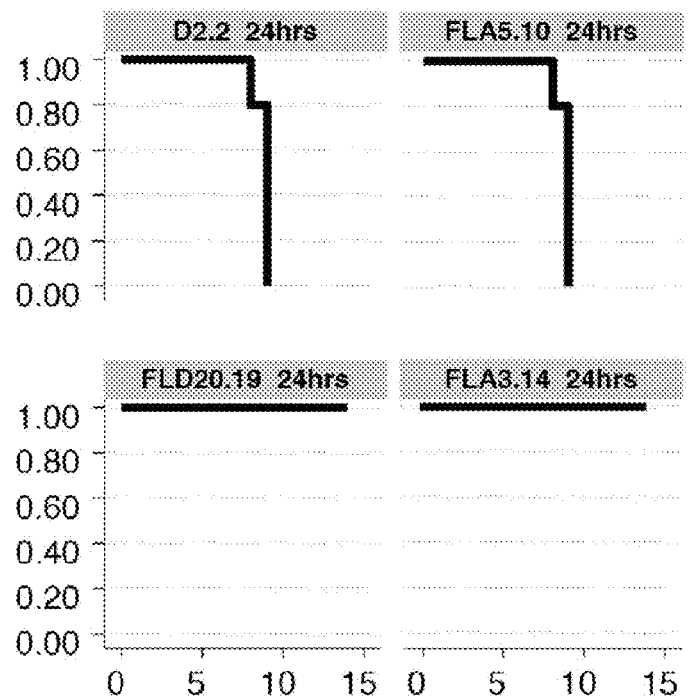
FIG. 5 shows the proportion of mice surviving (%) over a 15 day period after infection (at day 0) in a serotherapy experiment (Kaplan-Meier survival curve) of BALB/c mice intranasally infected 24 hours previously with A/Indonesia/5/05.

Attenuation of established infection represents a clinically relevant endpoint for anti-viral therapy against H5N1 infection. To this end, the efficacy of treatment with FLA3.14, FLA5.10, FLD20.19 and FLD21.140 (injected i.p at 1 mg/mouse) was determined in BALB/c mice intranasally infected 24, 48 or 72 hours previously with 5 $LD_{50}$ of A/Vietnam/1203/04. FIG. 4 shows that FLA3.14, FLA5.10, FLD20.19 and FLD21.140 provided robust protection from lethality in A/Vietnam/1203/04 infected mice at all time points, while the control (D2.2) gave no protection. The therapeutic efficacy of antibodies FLA3.14, FLA5.10 and FLD20.19 was also assessed against A/Indonesia/5/05, an antigenically divergent H5N1 virus from clade 2. FIG. 5 shows that FLA3.14 and FLD20.19 provided robust protection from lethality in A/Indonesia/5/05 infected mice when given 24 hrs after virus challenge, whilst FLA5.10 and the control (D2.2) gave no protection, consistent with the in vitro neutralization data (see above). These data provide proof of concept that monoclonal antibody therapy for at least up to 72 hrs post-infection in the mouse model can markedly improve survival from highly virulent H5N1 infection. Importantly, these data also imply it is possible to obtain significant cross-protection against a clade 2 H5N1 virus using an antibody elicited by a clade 1 virus e.g. via a shared epitope.

Breadth of Reactivity of Monoclonal Antibodies Against a Panel of H5N1 Viruses

The breadth of cross-reactivity of neutralising monoclonal antibodies was assessed using retroviral pseudotypes [50]. Pseudotypes containing the full length HA open reading frame from clades 1, 2.1, 2.2 and 2.3 of H5N1 influenza A viruses were used. Data represent $IC_{50}$ values expressed in ng/ml:

| Clade | HK/213/03 1 | VN/1203/04 1 | VN/1194.04 1 | IN/5/05 2.1 | WS/Mong/244/05 2.2 | TY/TY/1/05 2.2 | Anhui/1/05 2.3 |
|---|---|---|---|---|---|---|---|
| | | | | Strain | | | |
| FLA3.14 | 33 | 65 | 86 | 12 | 67 | 76 | 172 |
| FLA5.10 | 2.5 | 24 | 26 | Nn | Nn | Nn | Nn |
| FLD20.19 | 10 | 16 | 13 | 77 | 4 | 10 | 104 |
| FLD21.119 | 0.7 | 5 | 7 | Nn | 22 | 5 | Nn |
| FLD84 | 14 | 42 | 17 | 30 | 30 | 32 | 118 |
| FLD93 | 11 | 48 | 22 | 59 | 11 | 13 | Nn |
| FLD122 | 2 | 5 | 6 | 4 | 6 | 8 | 19 |
| FLS127 | 750 | 13 | 19 | Nn | Nn | Nn | Nn |
| FLD129 | 0.5 | 1.7 | 1.2 | 678 | 3 | 6 | 16 |
| FLD132 | 0.5 | 1 | 1.6 | Nn | 1 | 1 | 1800 |
| FLD194 | 2 | 5 | 4 | 5 | 3 | 5 | 2 |

Nn: Not neutralizing

In addition to FLD20.19, two other mAbs (FLD122 and FLD194) show high breadth of reactivity being able to neutralise with high potency all tested viruses from the different clades.

Antibody Characterisation

The genes encoding the heavy and light chains of antibodies FLA5.10, FLD21.140, FLA3.14 and FLD20.19 were sequenced (SEQ ID NOs 2, 4, 6, 8, 10, 12, 14 and 16). The encoded amino acid sequences were inferred (SEQ ID NOs 1, 3, 5, 7, 9, 11, 13, 15) and the CDR residues were identified using the IMGT numbering system [19-21] (SEQ ID NOs 17 to 40).

The genes encoding the heavy and light chains of antibodies FLD84, FLD93, FLD122, FLD127, FLD129, FLD132 and FLD194 were sequenced (SEQ ID NOs 41, 43, 51, 53, 61, 63, 71, 73, 81, 83, 91, 93, 101, 103). The encoded amino acid sequences were inferred (SEQ ID NOs 42, 44, 52, 54, 62, 64, 72, 74, 82, 84, 92, 94, 102, 104) and the CDR residues were identified using the IMGT numbering system [19-21] (SEQ ID NOs 45-50, 55-60, 65-70, 75-80, 85-90, 95-100, 105-110).

Cross-inhibition experiments were used to identify antibodies of non-overlapping specificities. Various antibodies were tested for competition against FLD20.19, FLA3.14 and FLD194.110 and % inhibitions were as follows:

| Competitor | Inhibition of binding (%) | | |
|---|---|---|---|
| | FLD20.19 | FLA3.14 | FLD194 |
| FLA3.14 | 0 | 100 | 100 |
| FLA5.10 | 100 | 0 | 100 |
| FLD20.19 | 100 | 0 | 0 |
| FLD21.119 | 100 | 0 | 0 |
| FLD84 | 100 | 0 | 0 |
| FLD93 | 100 | 0 | 0 |
| FLD122 | 100 | 65 | 100 |
| FLD127 | 100 | 0 | 0 |
| FLD129 | 100 | 0 | 100 |
| FLD132 | 0 | 0 | 52 |
| FLD194 | 0 | 0 | 100 |

Thus FLD20.19 and FLD194 do not cross-compete for binding to HA, and so they should recognize distinct non-overlapping epitopes. These antibodies may thus be used in combination for containment of virus escape mutants.

It will be understood that the invention has been described by way of example only and modifications may be made whilst remaining within the scope and spirit of the invention.

REFERENCES

The Contents of which are Hereby Incorporated by Reference

[1] Hanson et al. (2006) *Respiratory Research* 7:126.
[2] WO2007/089753.

[3] WHO document: *Antigenic and genetic characteristics of H5N1 viruses and candidate H5N1 vaccine viruses developed for potential use as pre-pandemic vaccines.*
[4] WO03/078600.
[5] Green (1999) *J Immunol Methods.* 231(1-2):11-23.
[6] Mancini et al. (2004) *New Microbiol.* 27(4):315-28.
[7] WO2004/076677.
[8] Traggiai et al. (2004) *Nat Med.* 10(8):871-5.
[9] Ewert et al. (2004) *Methods* 34(2):184-99.
[10] Riechmann et al. (1988) *Nature* 332:323-327.
[11] O'Brien & Jones (2003) *Methods Mol Biol.* 207:81-100.
[12] Iwahashi et al. (1999) *Mol Immunol.* 36(15-16):1079-91.
[13] Lo (2004) *Methods Mol Biol.* 248:135-59.
[14] Verhoeyen et al. (1988) *Science* 239: 1534-1536.
[15] Kashmiri et al. (2005) *Methods* 36(1):25-34.
[16] Gonzales et al. (2004) *Mol Immunol.* 41(9):863-72.
[17] Kabat et al. (1991) *Sequences of Proteins of Immunological Interest,* 5th Ed. Public Health Service, National Institutes of Health, Bethesda, Md.
[18] Chothia & Lesk (1987) *Mol. Biol.* 196:901-917.
[19] Lefranc et al. (1997) *Immunol Today* 18:509.
[20] Lefranc et al. (1999) *The Immunologist* 7:132-6.
[21] Lefranc et al. (2003) *Dev Comp Immunol* 27:55-77.
[22] WO02/46235.
[23] Worn & Pluckthun (2001) *J Mol Biol.* 305(5):989-1010.
[24] WO93/16185
[25] Adams & Schier (1999) *J Immunol Methods.* 231(1-2): 249-60.
[26] Hallborn & Carlsson (2002) *Biotechniques* Suppl:30-7.
[27] Pini & Bracci (2000) *Curr Protein Pept Sci* 1(2):155-69.
[28] Walter et al. (2001) *Comb Chem High Throughput Screen.* 4(2):193-205.
[29] Gruber et al. (1994) *J Immunol* 152(11):5368-74.
[30] U.S. Pat. No. 5,591,828
[31] WO 93/11161.
[32] Hollinger et al. (1993) *Proc. Natl. Acad. Sci. USA* 90:6444-6448.
[33] Hudson & Kortt (1999) *J Immunol Methods* 231:177-89.
[34] Muyldermans (2001) *J Biotechnol* 74(4):277-302.
[35] Dumoulin et al. (2002) *Protein Sci.* 11(3):500-15.
[36] Sidhu et al. (2004) *J Mol Biol.* 338(2):299-310.
[37] Kotz et al. (2004) *Eur J Biochem.* 271(9):1623-9.
[38] WO2007/052242.
[39] U.S. Pat. No. 5,624,821.
[40] U.S. Pat. No. 6,737,056.
[41] U.S. Pat. No. 6,538,124.
[42] U.S. Pat. No. 6,528,624.
[43] Shields et al. (2001) *J Biol Chem* 276:6591-604.
[44] WO2006/033386.
[45] Idusogie et al. (2000) *J Immunol* 164(8):4178-84.
[46] Dall'acqua et al. (2006) *J Biol Chem* 281(33):23514-24.
[47] Marks et al. (1992) *Bio/Technology* 10:779-83.
[48] Wu et al. (2005) *J Mol Biol* 350(1):126-44.
[49] WO2007/021002.
[50] Temperton et al. (2007) *Influenza and other Respiratory Viruses.* DOI: 10.1111/j.1750-2659.2007.00016.x.
[51] Chapter 4 of *Kuby Immunology* (4th edition, 2000; ASIN: 0716733315
[52] Jones et al. *Biotechnol Prog* 2003, 19(1):163-8
[53] Cho et al. *Cytotechnology* 2001, 37:23-30
[54] Cho et al. *Biotechnol Prog* 2003, 19:229-32
[55] Gennaro (2000) *Remington: The Science and Practice of Pharmacy.* 20th edition, ISBN: 0683306472.
[56] U.S. Pat. No. 7,132,100.
[57] Simmons et al. (2007) PLoS Medicine 4:e178.
[58] Rowe et al. (1999) *J Clin Microbiol* 37(4):937-43.

The invention claimed is:

1. An isolated antibody, or an antigen binding fragment thereof, that neutralizes a H5N1 strain of influenza A virus comprising the heavy chain CDR1, CDR2 and CDR3 and the light chain CDR1, CDR2, and CDR3 sequences as set forth in SEQ ID NOs: 17-22, 23-28, 29-34, 35-40, 45-50, 55-60, 65-70, 75-80, 85-90, 95-100, or 105-110, respectively.

2. The antibody of claim 1, or an antigen binding fragment thereof, which binds to hemagglutinin present in the virion of a H5N1 strain of influenza A virus.

3. The antibody of claim 1, or an antigen binding fragment thereof, wherein said antibody comprises a heavy chain variable region comprising SEQ ID NO: 13 and a light chain variable region comprising SEQ ID NO: 15.

4. The antibody of claim 1, or an antigen binding fragment thereof, wherein said antibody comprises a heavy chain variable region comprising SEQ ID NO: 5 and a light chain variable region comprising SEQ ID NO: 7.

5. The antibody of claim 1, or an antigen binding fragment thereof, wherein said antibody comprises a heavy chain variable region comprising SEQ ID NO: 9 and a light chain variable region comprising SEQ ID NO: 11.

6. The antibody of claim 1, or an antigen binding fragment thereof, wherein said antibody comprises a heavy chain variable region comprising SEQ ID NO: 1 and a light chain variable region comprising SEQ ID NO: 3.

7. The antibody of claim 1, or an antigen binding fragment thereof, wherein said antibody comprises a heavy chain variable region comprising SEQ ID NO: 42 and a light chain variable region comprising SEQ ID NO: 44.

8. The antibody of claim 1, or an antigen binding fragment thereof, wherein said antibody comprises a heavy chain variable region comprising SEQ ID NO: 52 and a light chain variable region comprising SEQ ID NO: 54.

9. The antibody of claim 1, or an antigen binding fragment thereof, wherein said antibody comprises a heavy chain variable region comprising SEQ ID NO: 62 and a light chain variable region comprising SEQ ID NO: 64.

10. The antibody of claim 1, or an antigen binding fragment thereof, wherein said antibody comprises a heavy chain variable region comprising SEQ ID NO: 72 and a light chain variable region comprising SEQ ID NO: 74.

11. The antibody of claim 1, or an antigen binding fragment thereof, wherein said antibody comprises a heavy chain variable region comprising SEQ ID NO: 82 and a light chain variable region comprising SEQ ID NO: 84.

12. The antibody of claim 1, or an antigen binding fragment thereof, wherein said antibody comprises a heavy chain variable region comprising SEQ ID NO: 92 and a light chain variable region comprising SEQ ID NO: 94.

13. The antibody of claim 1, or an antigen binding fragment thereof, wherein said antibody comprises a heavy chain variable region comprising SEQ ID NO: 102 and a light chain variable region comprising SEQ ID NO: 104.

14. The antibody of claim 1, or an antigen binding fragment thereof, wherein the antibody is selected from the group consisting of FLA5.10, FLD21.140, FLA3.14, FLD20.19, FLD84, FLD93, FLD122, FLD127, FLD129, FLD132 and FLD194.

15. The antibody of claim 1, wherein the antibody has a λ light chain.

16. The antibody of claim 1, wherein the antibody does not have a IgG1 heavy chain.

17. A pharmaceutical composition comprising a first antibody, or an antigen binding fragment thereof, of claim 1, and a second, different antibody, or an antigen binding fragment thereof, wherein the first and second antibodies do not cross-compete with each other.

18. The antibody of claim 1, or a fragment thereof, wherein said antibody is a monoclonal antibody or a human antibody.

19. An antibody, or an antigen binding fragment thereof, wherein the antibody comprises a heavy chain variable region comprising the amino acid sequence of SEQ ID NO: 13 and a light chain variable region comprising the amino acid sequence of SEQ ID NO: 15; or a heavy chain variable region comprising the amino acid sequence of SEQ ID NO: 5 and a light chain variable region comprising the amino acid sequence of SEQ ID NO: 7; or a heavy chain variable region comprising the amino acid sequence of SEQ ID NO: 9 and a light chain variable region comprising the amino acid sequence of SEQ ID NO: 11; or a heavy chain variable region comprising the amino acid sequence of SEQ ID NO: 1 and a light chain variable region comprising the amino acid sequence of SEQ ID NO: 3; or a heavy chain variable region comprising the amino acid sequence of SEQ ID NO: 42 and a light chain variable region comprising the amino acid sequence of SEQ ID NO: 44; or a heavy chain variable region comprising the amino acid sequence of SEQ ID NO: 52 and a light chain variable region comprising the amino acid sequence of SEQ ID NO: 54; or a heavy chain variable region comprising the amino acid sequence of SEQ ID NO: 62 and a light chain variable region comprising the amino acid sequence of SEQ ID NO: 64; or a heavy chain variable region comprising the amino acid sequence of SEQ ID NO: 72 and a light chain variable region comprising the amino acid sequence of SEQ ID NO: 74; or a heavy chain variable region comprising the amino acid sequence of SEQ ID NO: 82 and a light chain variable region comprising the amino acid sequence of SEQ ID NO: 84; or a heavy chain variable region comprising the amino acid sequence of SEQ ID NO: 92 and a light chain variable region comprising the amino acid sequence of SEQ ID NO: 94; or a heavy chain variable region comprising the amino acid sequence of SEQ ID NO: 102 and a light chain variable region comprising the amino acid sequence of SEQ ID NO: 104, wherein the antibody or antigen binding fragment neutralizes a H5N1 strain of influenza A virus.

20. A pharmaceutical composition comprising two monoclonal antibodies of claim 1, or antigen binding fragments thereof, wherein the antibodies do not cross-compete with each other.

* * * * *

SEQUENCE LISTING

```
<160> NUMBER OF SEQ ID NOS: 110

<210> SEQ ID NO 1
<211> LENGTH: 129
<212> TYPE: PRT
<213> ORGANISM: Homo sapiens

<400> SEQUENCE: 1

Gln Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Ser Asn Tyr
            20                  25                  30

Gly Ile Ser Trp Val Arg Gln Ala Pro Gly Gln Gly Leu Asp Trp Met
        35                  40                  45

Gly Gly Ile Ile Pro Leu Phe Gly Thr Ala Asn Tyr Ala Gln Lys Phe
    50                  55                  60

Gln Gly Arg Val Thr Ile Thr Ala Asp Glu Ser Thr Ser Ser Ser Asn
65                  70                  75                  80

Met Glu Leu Ser Ser Leu Arg Ser Glu Asp Thr Ala Val Tyr Tyr Cys
                85                  90                  95

Ala Arg Asp Val His Asn Tyr Asp Phe Leu Thr Gly Tyr Pro Leu His
            100                 105                 110

Leu Tyr Gly Met Asp Val Trp Gly Gln Gly Thr Thr Val Thr Val Ser
        115                 120                 125

Ser
```

<210> SEQ ID NO 2
<211> LENGTH: 388
<212> TYPE: DNA
<213> ORGANISM: Homo sapiens

<400> SEQUENCE: 2

```
caggtgcagc tggtgcagtc tggggctgag gtgaagaagc ctgggtcctc ggtgacggtc    60
tcctgcaagg cttctggagg caccttcagc aattatggta tcagttgggt gcgacaggcc   120
cctggacaag gtcttgattg gatgggaggg atcatccctt tgtttggaac agcaaactac   180
gcacagaagt tccagggcag agtcacgatt accgcggacg aatccacgag ctcctccaac   240
atggagctga gcagcctgag atctgaggac acggccgtgt attactgtgc gagagatgtc   300
cacaattacg attttttgac tggttatcca cttcatctct acggtatgga cgtctggggc   360
caagggacca cggtcaccgt ctcctcag                                      388
```

<210> SEQ ID NO 3
<211> LENGTH: 107
<212> TYPE: PRT
<213> ORGANISM: Homo sapiens

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Ile Pro Pro Lys Leu Leu Ile
        35                  40                  45

Asn Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Thr Tyr Ser Ser Pro Pro
                85                  90                  95

Thr Phe Gly Gln Gly Thr Lys Val Glu Ile Lys
            100                 105
```

<210> SEQ ID NO 4
<211> LENGTH: 322
<212> TYPE: DNA
<213> ORGANISM: Homo sapiens

<400> SEQUENCE: 4

```
gacatccaga tgacccagtc tccatcctcc ctgtctgcat ctgtaggaga cagagtcacc    60
atcacttgcc gggcaagtca gagcattagc acctatttaa attggtatca gcagaaacca   120
ggaatacccc caaagctcct gatcaatgtt gcatccagtt tgcaaagtgg gtcccatca    180
aggttcagtg gcagtggatc tgggacagat ttcactctca ccatcagcag tctgcaacct   240
gaagattttg caagttacta ttgtcaacag acttacagtt cccctccaac gttcggccaa   300
gggaccaagg tggaaatcaa ac                                           322
```

<210> SEQ ID NO 5
<211> LENGTH: 125
<212> TYPE: PRT
<213> ORGANISM: Homo sapiens

<400> SEQUENCE: 5

Gln Val Gln Leu Gln Glu Ser Gly Pro Gly Leu Val Lys Pro Ser Gln

```
                1               5              10             15

Thr Leu Ser Leu Thr Cys Thr Val Ser Gly Gly Ser Ile Ser Ser Gly
                        20                  25                  30

Thr Tyr Tyr Trp Ser Trp Ile Arg His His Pro Gly Lys Gly Leu Glu
                        35                  40                  45

Trp Ile Gly Tyr Ile Tyr His Ser Gly Ser Ala Tyr Tyr Asn Pro Ser
                        50                  55                  60

Leu Glu Ser Arg Val Thr Met Ser Val Asp Thr Ser Lys Asn Gln Phe
             65                 70                  75                  80

Ser Leu Lys Leu Ser Ser Val Thr Ala Ala Asp Thr Ala Ile Tyr Tyr
                        85                  90                  95

Cys Ala Arg Ala Glu Asn Leu Leu Ser Pro Tyr Leu Ala Glu Gly Phe
                       100                 105                 110

Asp Pro Trp Gly Gln Gly Thr Leu Val Thr Val Ser Ser
                       115                 120                 125

<210> SEQ ID NO 6
<211> LENGTH: 376
<212> TYPE: DNA
<213> ORGANISM: Homo sapiens

<400> SEQUENCE: 6
caggtgcagc tgcaggagtc gggcccagga ctggtgaagc cttcgcagac cctgtccctc      60
acctgcactg tctctggtgg ctccatcagc agtgggactt actactggag ctggatccgc     120
catcacccag ggaagggcct ggagtggatt gggtacatct atcacagtgg gagcgcctac     180
tacaatccgt ccctcgagag tcgagttacc atgtcagtag acacgtctaa gaatcagttc     240
tccctgaagc tgagctctgt gactgccgcg gacacggcca tatattactg tgcgagagct     300
gagaatcttt tgtctcctta tttagccgag ggcttcgacc cctggggcca gggaaccctg     360
gtcaccgtct cctcag                                                    376

<210> SEQ ID NO 7
<211> LENGTH: 111
<212> TYPE: PRT
<213> ORGANISM: Homo sapiens

<400> SEQUENCE: 7

Gln Ser Val Leu Thr Gln Pro Pro Ser Ala Ser Gly Thr Pro Gly Gln
 1               5                  10                  15

Arg Val Thr Ile Ser Cys Ser Gly Ser Thr Ser Asn Ile Gly Ser Asn
            20                  25                  30

Ala Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
            50                  55                  60

Gly Ser Lys Ser Gly Thr Ser Ala Ser Leu Ala Ile Ser Gly Leu Gln
 65                 70                  75                  80

Ser Glu Asp Glu Ala Asp Tyr Tyr Cys Ala Ala Trp Asp Asp Ser Leu
            85                  90                  95

Ser Gly Ser Trp Val Phe Gly Gly Gly Thr Lys Leu Thr Val Leu
           100                 105                 110

<210> SEQ ID NO 8
<211> LENGTH: 334
<212> TYPE: DNA
<213> ORGANISM: Homo sapiens
```

<400> SEQUENCE: 8

```
cagtctgtgc tgactcagcc accctcagcg tctgggaccc ccgggcagag ggtcaccatc    60
tcttgttctg gaagcacctc aacatcgga agtaatgctg taaactggta ccagcagctc   120
ccaggaacgg cccccaaact cctcatctat agtaataatc agcggccctc aggggtccct   180
gaccgattct ctggctccaa gtctggcacc tcagcctccc tggccatcag tgggctccag   240
tctgaggatg aggctgatta ctactgtgca gcatgggatg acagcctgag tggttcttgg   300
gtgttcggcg agggaccaa gctgaccgtc ctag                               334
```

<210> SEQ ID NO 9
<211> LENGTH: 125
<212> TYPE: PRT
<213> ORGANISM: Homo sapiens

<400> SEQUENCE: 9

```
Glu Val Gln Leu Val Gln Ser Gly Ala Glu Val Lys Lys Pro Gly Glu
1               5                   10                  15
Ser Leu Lys Ile Ser Cys Gln Ala Ser Gly Tyr Ser Phe Thr Ser Arg
            20                  25                  30
Trp Ile Gly Trp Val Arg Gln Met Pro Gly Lys Gly Leu Glu Trp Val
        35                  40                  45
Gly Phe Ile Tyr Pro Ser Asp Ser Asp Val Arg Tyr Ser Pro Ser Phe
    50                  55                  60
Arg Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Phe Cys
                85                  90                  95
Ala Arg Leu Gly Gly Asn Lys Asp Tyr Gly Asp Tyr Leu Trp Tyr Phe
            100                 105                 110
Asp Leu Trp Gly Arg Gly Ala Leu Val Thr Val Ser Ser
        115                 120                 125
```

<210> SEQ ID NO 10
<211> LENGTH: 376
<212> TYPE: DNA
<213> ORGANISM: Homo sapiens

<400> SEQUENCE: 10

```
gaggtgcagc tggtgcagtc tggagcagag gtgaaaaagc ccggggagtc tctgaagatc    60
tcctgtcagg cgtctggata cagctttacc agccgctgga tcggctgggt gcgccagatg   120
cccgggaaag gcctggagtg ggtgggattc atctatccta gtgactctga tgttagatat   180
agtccgtcct tcagaggcca ggtcaccatc tcagccgaca gtccatcag caccgcctac   240
ctacagtgga gcagcctgaa ggcctcggac accgccatgt atttctgtgc gagacttggg   300
ggaaataagg actacggtga ctacctctgg tacttcgatc tctggggccg tggcgccctg   360
gtcactgtct cctcag                                                   376
```

<210> SEQ ID NO 11
<211> LENGTH: 106
<212> TYPE: PRT
<213> ORGANISM: Homo sapiens

<400> SEQUENCE: 11

```
Glu Ile Val Met Thr Gln Ser Pro Asp Thr Leu Ser Val Ser Pro Gly
1               5                   10                  15
Glu Arg Ala Thr Leu Ser Cys Arg Ala Ser Gln Ser Val Asn Arg Arg
```

```
                    20                  25                  30
Leu Ala Trp Tyr Gln Gln Lys Pro Gly Gln Ala Pro Arg Leu Leu Ile
            35                  40                  45

His Asp Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asn Trp Leu Ser
                    85                  90                  95

Phe Gly Gln Gly Thr Arg Leu Glu Ile Lys
                100                 105

<210> SEQ ID NO 12
<211> LENGTH: 319
<212> TYPE: DNA
<213> ORGANISM: Homo sapiens

<400> SEQUENCE: 12
gaaatagtga tgacgcagtc tccagacacc ctgtctgtgt ctccaggaga aagagccacc      60
ctctcctgca gggccagtca gagtgttaac aggaggttag cctggtacca gcagaaacct     120
ggccaggctc ccaggctcct catccatgat gcatccacca gggccactgg tatcccagcc     180
aggttcagtg gcagtgggtc tgggacagag ttcactctca ccatcagcag cctgcagtct     240
gaagattttg cagtttatta ctgtcagcag tatgataact ggctctcctt cggccagggg     300
acacgactgg agattaaac                                                  319

<210> SEQ ID NO 13
<211> LENGTH: 120
<212> TYPE: PRT
<213> ORGANISM: Homo sapiens

<400> SEQUENCE: 13

Gln Val Gln Leu Val Gln Ser Gly Ala Glu Val Lys Glu Pro Gly Ser
1               5                   10                  15

Ala Met Lys Val Ser Cys Lys Ala Ser Gly Gly Thr Phe Ser Ser Asp
                20                  25                  30

Ala Phe Cys Trp Val Arg Gln Ala Pro Gly Arg Gly Leu Glu Trp Met
            35                  40                  45

Gly Gly Ile Ile Pro Val Phe Gln Thr Ala Asn Tyr Gly Pro Asn Phe
        50                  55                  60

Gln Gly Arg Val Thr Ile Ser Ala Asp Val Tyr Thr Thr Thr Leu Tyr
65                  70                  75                  80

Leu Glu Leu Ser Gly Leu Thr Ser Glu Asp Thr Ala Val Tyr Phe Cys
                    85                  90                  95

Ala Arg Ser Gly Asp Gly Tyr Asn Tyr Tyr Phe Pro Leu Trp Gly Gln
                100                 105                 110

Gly Thr Leu Val Thr Val Ser Ser
                115                 120

<210> SEQ ID NO 14
<211> LENGTH: 361
<212> TYPE: DNA
<213> ORGANISM: Homo sapiens

<400> SEQUENCE: 14
caggtgcagc tggtgcagtc tggggctgaa gtgaaggagc ctgggtccgc gatgaaggtc      60
tcctgcaagg cctctggagg caccttcagt agtgatgcct tctgctgggt gcgacaggcc     120
```

```
cctggacgag ggcttgagtg gatgggaggg atcatccctg tctttcaaac tgcaaactac    180
ggaccgaact tccagggcag agtcaccatt agcgcggacg tttacacgac cacgctttac    240
ctggaattga gtggcctgac atctgaggac acggccgtgt attttgtgc gagatccggg    300 gatggctaca actactactt tcccctctgg ggccagggaa ccctggtcac cgtctcctca    360
g                                                                    361
```

<210> SEQ ID NO 15
<211> LENGTH: 107
<212> TYPE: PRT
<213> ORGANISM: Homo sapiens

<400> SEQUENCE: 15

```
Asp Ile Gln Met Thr Gln Ser Pro Ser Thr Leu Ser Gly Ser Val Gly
1               5                   10                  15

Asp Arg Val Thr Ile Thr Cys Arg Ala Ser Gln Asn Ile Gly Pro Trp
            20                  25                  30

Leu Ala Trp Tyr Gln Gln Glu Ser Gly Lys Ala Pro Lys Leu Leu Ile
        35                  40                  45

Ser Arg Ala Ser Ile Leu Glu Ser Gly Val Pro Ser Arg Phe Ser Gly
    50                  55                  60

Thr Gly Thr Gly Thr Glu Phe Thr Leu Thr Ile Ser Ser Leu Gln Pro
65                  70                  75                  80

Asp Asp Phe Ala Thr Tyr Tyr Cys Gln His Tyr Asn Ala Tyr Trp Gly
                85                  90                  95

Thr Phe Gly Gln Gly Thr Lys Val Glu Ile Asn
            100                 105
```

<210> SEQ ID NO 16
<211> LENGTH: 321
<212> TYPE: DNA
<213> ORGANISM: Homo sapiens

<400> SEQUENCE: 16

```
gacatccaga tgacccagtc tccttccacc ctgtctggat cagtaggaga cagagtcacc    60
atcacttgcc gggccagtca gaatattggt ccctggttgg cctggtacca acaagaatca    120
gggaaagccc ctaagctcct gatctctagg gcgtctattt tagaaagtgg ggtcccatca    180
agattcagcg gcactggaac tgggacagaa ttcactctca ccatcagcag cctgcagcct    240
gatgattttg caacttatta ctgccaacac tataatgctt attgggggac gttcggccaa    300
gggaccaagg tggaaatcaa c                                              321
```

<210> SEQ ID NO 17
<211> LENGTH: 8
<212> TYPE: PRT
<213> ORGANISM: Homo sapiens

<400> SEQUENCE: 17

```
Gly Gly Thr Phe Ser Ser Asp Ala
1               5
```

<210> SEQ ID NO 18
<211> LENGTH: 8
<212> TYPE: PRT
<213> ORGANISM: Homo sapiens

<400> SEQUENCE: 18

```
Ile Ile Pro Val Phe Gln Thr Ala
```

```
<210> SEQ ID NO 19
<211> LENGTH: 13
<212> TYPE: PRT
<213> ORGANISM: Homo sapiens

<400> SEQUENCE: 19

Ala Arg Ser Gly Asp Gly Tyr Asn Tyr Tyr Phe Pro Leu
1               5                   10

<210> SEQ ID NO 20
<211> LENGTH: 6
<212> TYPE: PRT
<213> ORGANISM: Homo sapiens

<400> SEQUENCE: 20

Gln Asn Ile Gly Pro Trp
1               5

<210> SEQ ID NO 21
<211> LENGTH: 3
<212> TYPE: PRT
<213> ORGANISM: Homo sapiens

<400> SEQUENCE: 21

Arg Ala Ser
1

<210> SEQ ID NO 22
<211> LENGTH: 9
<212> TYPE: PRT
<213> ORGANISM: Homo sapiens

<400> SEQUENCE: 22

Gln His Tyr Asn Ala Tyr Trp Gly Thr
1               5

<210> SEQ ID NO 23
<211> LENGTH: 10
<212> TYPE: PRT
<213> ORGANISM: Homo sapiens

<400> SEQUENCE: 23

Gly Gly Ser Ile Ser Ser Gly Thr Tyr Tyr
1               5                   10

<210> SEQ ID NO 24
<211> LENGTH: 7
<212> TYPE: PRT
<213> ORGANISM: Homo sapiens

<400> SEQUENCE: 24

Ile Tyr His Ser Gly Ser Ala
1               5

<210> SEQ ID NO 25
<211> LENGTH: 17
<212> TYPE: PRT
<213> ORGANISM: Homo sapiens

<400> SEQUENCE: 25

Ala Arg Ala Glu Asn Leu Leu Ser Pro Tyr Leu Ala Glu Gly Phe Asp
1               5                   10                  15

Pro
```

```
<210> SEQ ID NO 26
<211> LENGTH: 8
<212> TYPE: PRT
<213> ORGANISM: Homo sapiens

<400> SEQUENCE: 26

Thr Ser Asn Ile Gly Ser Asn Ala
1               5

<210> SEQ ID NO 27
<211> LENGTH: 3
<212> TYPE: PRT
<213> ORGANISM: Homo sapiens

<400> SEQUENCE: 27

Ser Asn Asn
1

<210> SEQ ID NO 28
<211> LENGTH: 12
<212> TYPE: PRT
<213> ORGANISM: Homo sapiens

<400> SEQUENCE: 28

Ala Ala Trp Asp Asp Ser Leu Ser Gly Ser Trp Val
1               5                   10

<210> SEQ ID NO 29
<211> LENGTH: 8
<212> TYPE: PRT
<213> ORGANISM: Homo sapiens

<400> SEQUENCE: 29

Gly Tyr Ser Phe Thr Ser Arg Trp
1               5

<210> SEQ ID NO 30
<211> LENGTH: 8
<212> TYPE: PRT
<213> ORGANISM: Homo sapiens

<400> SEQUENCE: 30

Ile Tyr Pro Ser Asp Ser Asp Val
1               5

<210> SEQ ID NO 31
<211> LENGTH: 18
<212> TYPE: PRT
<213> ORGANISM: Homo sapiens

<400> SEQUENCE: 31

Ala Arg Leu Gly Gly Asn Lys Asp Tyr Gly Asp Tyr Leu Trp Tyr Phe
1               5                   10                  15

Asp Leu

<210> SEQ ID NO 32
<211> LENGTH: 6
<212> TYPE: PRT
<213> ORGANISM: Homo sapiens

<400> SEQUENCE: 32

Gln Ser Val Asn Arg Arg
1               5
```

```
<210> SEQ ID NO 33
<211> LENGTH: 3
<212> TYPE: PRT
<213> ORGANISM: Homo sapiens

<400> SEQUENCE: 33

Asp Ala Ser
1

<210> SEQ ID NO 34
<211> LENGTH: 8
<212> TYPE: PRT
<213> ORGANISM: Homo sapiens

<400> SEQUENCE: 34

Gln Gln Tyr Asp Asn Trp Leu Ser
1               5

<210> SEQ ID NO 35
<211> LENGTH: 8
<212> TYPE: PRT
<213> ORGANISM: Homo sapiens

<400> SEQUENCE: 35

Gly Gly Thr Phe Ser Asn Tyr Gly
1               5

<210> SEQ ID NO 36
<211> LENGTH: 8
<212> TYPE: PRT
<213> ORGANISM: Homo sapiens

<400> SEQUENCE: 36

Ile Ile Pro Leu Phe Gly Thr Ala
1               5

<210> SEQ ID NO 37
<211> LENGTH: 22
<212> TYPE: PRT
<213> ORGANISM: Homo sapiens

<400> SEQUENCE: 37

Ala Arg Asp Val His Asn Tyr Asp Phe Leu Thr Gly Tyr Pro Leu His
1               5                   10                  15

Leu Tyr Gly Met Asp Val
            20

<210> SEQ ID NO 38
<211> LENGTH: 6
<212> TYPE: PRT
<213> ORGANISM: Homo sapiens

<400> SEQUENCE: 38

Gln Ser Ile Ser Thr Tyr
1               5

<210> SEQ ID NO 39
<211> LENGTH: 3
<212> TYPE: PRT
<213> ORGANISM: Homo sapiens

<400> SEQUENCE: 39

Val Ala Ser
1
```

```
<210> SEQ ID NO 40
<211> LENGTH: 9
<212> TYPE: PRT
<213> ORGANISM: Homo sapiens

<400> SEQUENCE: 40

Gln Gln Thr Tyr Ser Ser Pro Pro Thr
 1               5

<210> SEQ ID NO 41
<211> LENGTH: 388
<212> TYPE: DNA
<213> ORGANISM: Homo sapiens

<400> SEQUENCE: 41
```

| | | | | | |
|---|---|---|---|---|---|
| caggtgcaac | tgcaggagtc | gggcccagga | ctggtgaagc | cttcggagac | cctgtccctc | 60 |
| atctgcgctg | tctctggtgc | ctccataagt | agttcttact | ggagctggat | tcggcagccc | 120 |
| ccagggaagg | gactggagtg | gattggatat | atctattaca | gtggggtcac | caaatacaac | 180 |
| ccctccctca | agagtcgagt | cacccttttct | gtggacacgt | ccaagaacca | cttctccctg | 240 |
| aagctgagct | atgtgaccgc | tgcggacacg | gccgtgtatt | actgtgcgag | aaatcttccg | 300 |
| gatattgcgg | tggtgactgc | tgttcaggat | gcgactccgg | tctggttcga | cccctggggc | 360 |
| ccgggcaccc | tggtctccgt | ctcctcag | | | | 388 |

```
<210> SEQ ID NO 42
<211> LENGTH: 129
<212> TYPE: PRT
<213> ORGANISM: Homo sapiens

<400> SEQUENCE: 42

Gln Val Gln Leu Gln Glu Ser Gly Pro Gly Leu Val Lys Pro Ser Glu
 1               5                  10                  15

Thr Leu Ser Leu Ile Cys Ala Val Ser Gly Ala Ser Ile Ser Ser Ser
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Val Thr Lys Tyr Asn Pro Ser Leu Lys
     50                  55                  60

Ser Arg Val Thr Leu Ser Val Asp Thr Ser Lys Asn His Phe Ser Leu
 65                  70                  75                  80

Lys Leu Ser Tyr Val Thr Ala Ala Asp Thr Ala Val Tyr Tyr Cys Ala
                 85                  90                  95

Arg Asn Leu Pro Asp Ile Ala Val Val Thr Ala Val Gln Asp Ala Thr
            100                 105                 110

Pro Val Trp Phe Asp Pro Trp Gly Pro Gly Thr Leu Val Ser Val Ser
        115                 120                 125

Ser

<210> SEQ ID NO 43
<211> LENGTH: 325
<212> TYPE: DNA
<213> ORGANISM: Homo sapiens

<400> SEQUENCE: 43
```

| | | | | | |
|---|---|---|---|---|---|
| gacatccagt | tgacccagtc | tccatcatcc | ctgtctgcat | ctgtaggaga | cagagtcacc | 60 |
| atcacttgcc | gggcaagtca | gggcattatc | acgtatttaa | attggtatca | gcagaaacca | 120 |
| gggaaagccc | ctaagctcct | gatctatgcg | acatacagtt | tgcaaaatgg | ggtcccatcg | 180 |

```
aggttcagtg gcagtggatc tgggacagat ttcactctca ccatcagcag tctgcaacct    240
gaagattttg caacttacta ctgtcaacag agttacagta gcctcatgtt cacttttggc    300 cagggggacca agctggacat caaac                                         325
```

<210> SEQ ID NO 44
<211> LENGTH: 108
<212> TYPE: PRT
<213> ORGANISM: Homo sapiens

<400> SEQUENCE: 44

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ile Thr Tyr
            20                  25                  30

Leu Asn Trp Tyr Gln Gln Lys Pro Gly Lys Ala Pro Lys Leu Leu Ile
        35                  40                  45

Tyr Ala Thr Tyr Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Leu Met
                85                  90                  95

Phe Thr Phe Gly Gln Gly Thr Lys Leu Asp Ile Lys
            100                 105
```

<210> SEQ ID NO 45
<211> LENGTH: 8
<212> TYPE: PRT
<213> ORGANISM: Homo sapiens

<400> SEQUENCE: 45

```
Gly Ala Ser Ile Ser Ser Ser Tyr
1               5
```

<210> SEQ ID NO 46
<211> LENGTH: 7
<212> TYPE: PRT
<213> ORGANISM: Homo sapiens

<400> SEQUENCE: 46

```
Ile Tyr Tyr Ser Gly Val Thr
1               5
```

<210> SEQ ID NO 47
<211> LENGTH: 23
<212> TYPE: PRT
<213> ORGANISM: Homo sapiens

<400> SEQUENCE: 47

```
Ala Arg Asn Leu Pro Asp Ile Ala Val Val Thr Ala Val Gln Asp Ala
1               5                   10                  15

Thr Pro Val Trp Phe Asp Pro
            20
```

<210> SEQ ID NO 48
<211> LENGTH: 6
<212> TYPE: PRT
<213> ORGANISM: Homo sapiens

<400> SEQUENCE: 48

Gln Gly Ile Ile Thr Tyr
1               5

<210> SEQ ID NO 49
<211> LENGTH: 3
<212> TYPE: PRT
<213> ORGANISM: Homo sapiens

<400> SEQUENCE: 49

Ala Thr Tyr
1

<210> SEQ ID NO 50
<211> LENGTH: 10
<212> TYPE: PRT
<213> ORGANISM: Homo sapiens

<400> SEQUENCE: 50

Gln Gln Ser Tyr Ser Ser Leu Met Phe Thr
1               5                   10

<210> SEQ ID NO 51
<211> LENGTH: 382
<212> TYPE: DNA
<213> ORGANISM: Homo sapiens

<400> SEQUENCE: 51

```
tggtggcagc tggtgcagtc tggggctgag gtgaagaagc ctgggtcctc ggtgaaggtc     60
tcctgcaagg cttctggagg caccttcagc agctatgata tcagctgggt gcgacaggcc    120
cctggacaag ggcttgagtg gatgggaggg atcatccctc tctatggcac agcaaactac    180
gcacagaagt tccagggcag agtcacgatc accgcggacg aatccacgag cacagcctac    240
atggagctga gcagcctgag atctgaggac acggccgttt attactgtgc gagagcaggt    300
ggtgatagta gtggttatta tggtgccttg gggcggttct tccagcactg gggccagggc    360
accctggtca ccgtctcctc ag                                             382
```

<210> SEQ ID NO 52
<211> LENGTH: 127
<212> TYPE: PRT
<213> ORGANISM: Homo sapiens

<400> SEQUENCE: 52

Trp Trp Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Asp Ile Ser Trp Val Arg Gln Ala Pro Gly Gln Gly Leu Glu Trp Met
        35                  40                  45

Gly Gly Ile Ile Pro Ile Tyr Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Gly Asp Ser Ser Gly Tyr Tyr Gly Ala Leu Gly Arg
            100                 105                 110

Phe Phe Gln His Trp Gly Gln Gly Thr Leu Val Thr Val Ser Ser
        115                 120                 125

-continued

```
<210> SEQ ID NO 53
<211> LENGTH: 322
<212> TYPE: DNA
<213> ORGANISM: Homo sapiens

<400> SEQUENCE: 53
gtcatctgga tgacccagtc tccatcttta ctctctgcat ctacaggaga cagagtcacc    60
atcagttgtc ggatgagtca gggcattagc agttatttag cctggtatca gcaaaaacca   120
gggaaagccc ctgagctcct gatccatact gcatacactt gaaaagtgg ggtcccatca    180 aggttcagtg gcagtggatc tgggaaagat ttcactctca ccatcagtgg cctgcagtct   240
gaagattttg caacttatta ctgtcaacag tattatagtt tcccgtacac ttttggccag   300
gggaccaagg tggagatcaa ac                                            322

<210> SEQ ID NO 54
<211> LENGTH: 107
<212> TYPE: PRT
<213> ORGANISM: Homo sapiens

<400> SEQUENCE: 54

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45

His Thr Ala Tyr Thr Leu Lys Ser Gly Val Pro Ser Arg Phe Ser Gly
    50                  55                  60

Ser Gly Ser Gly Lys Asp Phe Thr Leu Thr Ile Ser Gly Leu Gln Ser
65                  70                  75                  80

Glu Asp Phe Ala Thr Tyr Tyr Cys Gln Gln Tyr Tyr Ser Phe Pro Tyr
                85                  90                  95

Thr Phe Gly Gln Gly Thr Lys Val Glu Ile Lys
            100                 105

<210> SEQ ID NO 55
<211> LENGTH: 8
<212> TYPE: PRT
<213> ORGANISM: Homo sapiens

<400> SEQUENCE: 55

Gly Gly Thr Phe Ser Ser Tyr Asp
1               5

<210> SEQ ID NO 56
<211> LENGTH: 8
<212> TYPE: PRT
<213> ORGANISM: Homo sapiens

<400> SEQUENCE: 56

Ile Ile Pro Ile Tyr Gly Thr Ala
1               5

<210> SEQ ID NO 57
<211> LENGTH: 20
<212> TYPE: PRT
<213> ORGANISM: Homo sapiens

<400> SEQUENCE: 57

Ala Arg Ala Gly Gly Asp Ser Ser Gly Tyr Tyr Gly Ala Leu Gly Arg
1               5                   10                  15
```

```
Phe Phe Gln His
           20

<210> SEQ ID NO 58
<211> LENGTH: 6
<212> TYPE: PRT
<213> ORGANISM: Homo sapiens

<400> SEQUENCE: 58

Gln Gly Ile Ser Ser Tyr
1               5

<210> SEQ ID NO 59
<211> LENGTH: 3
<212> TYPE: PRT
<213> ORGANISM: Homo sapiens

<400> SEQUENCE: 59

Thr Ala Tyr
1

<210> SEQ ID NO 60
<211> LENGTH: 9
<212> TYPE: PRT
<213> ORGANISM: Homo sapiens

<400> SEQUENCE: 60

Gln Gln Tyr Tyr Ser Phe Pro Tyr Thr
1               5

<210> SEQ ID NO 61
<211> LENGTH: 370
<212> TYPE: DNA
<213> ORGANISM: Homo sapiens

<400> SEQUENCE: 61
cagtttcaac tggtgcagtc tggacctgag gtgaagaagc ctgggacctc agtgaaggtc      60
tcctgcaagg cctctggcta cacttccacc acctacggga tcagctgggt gcgacaggtc     120
cctggacaag gcttgagtg gatgggatgg atcaaccctt acaacggaaa cccacattat      180
ggacagaagt tccagggcag agtcaccttg accagagaca catccacaaa tactgcctac     240
ctggaaatat tgagcctcag atctgacgac acggccgtct attactgtgc gagagatggg     300
tggggccagc aactggttcc ctattacttt gactactggg gccagggaac cctggtcacc     360
gtctcctcag                                                            370

<210> SEQ ID NO 62
<211> LENGTH: 123
<212> TYPE: PRT
<213> ORGANISM: Homo sapiens

<400> SEQUENCE: 62

Gln Phe Gln Leu Val Gln Ser Gly Pro Glu Val Lys Lys Pro Gly Thr
1               5                   10                  15

Ser Val Lys Val Ser Cys Lys Ala Ser Gly Tyr Thr Ser Thr Thr Tyr
            20                  25                  30

Gly Ile Ser Trp Val Arg Gln Val Pro Gly Gln Gly Leu Glu Trp Met
        35                  40                  45

Gly Trp Ile Asn Pro Tyr Asn Gly Asn Pro His Tyr Gly Gln Lys Phe
    50                  55                  60

Gln Gly Arg Val Thr Leu Thr Arg Asp Thr Ser Thr Asn Thr Ala Tyr
```

```
                        65                  70                  75                  80
Leu Glu Ile Leu Ser Leu Arg Ser Asp Asp Thr Ala Val Tyr Tyr Cys
                    85                  90                  95

Ala Arg Asp Gly Trp Gly Gln Gln Leu Val Pro Tyr Tyr Phe Asp Tyr
                100                 105                 110

Trp Gly Gln Gly Thr Leu Val Thr Val Ser Ser
                115                 120

<210> SEQ ID NO 63
<211> LENGTH: 337
<212> TYPE: DNA
<213> ORGANISM: Homo sapiens

<400> SEQUENCE: 63
gatattgtga tgactcagtc tccactctcc ctgcccgtca cccctggaga gccggcctcc        60
atctcctgca gggctagtca gagcctcctg catagtaatg gatacaacta tttggattgg       120
tacctgcaga agccagggca gtctccacag ctcctgattc agttgggttc tactcgggcc       180
tccggggtcc ctgacaggtt cagtggcagt ggatcaggca cagatttcac actcgaaatc       240
agcagagtgg aggctgagga tgttggggtt tattactgca tgcaagctct acaacttccc       300
ctcgccttcg gccaagggac acgactggag attaaac                                337

<210> SEQ ID NO 64
<211> LENGTH: 112
<212> TYPE: PRT
<213> ORGANISM: Homo sapiens

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Gln Leu Gly Ser Thr Arg Ala Ser Gly Val Pro
        50                  55                  60

Asp Arg Phe Ser Gly Ser Gly Ser Gly Thr Asp Phe Thr Leu Glu Ile
65                  70                  75                  80

Ser Arg Val Glu Ala Glu Asp Val Gly Val Tyr Tyr Cys Met Gln Ala
                85                  90                  95

Leu Gln Leu Pro Leu Ala Phe Gly Gln Gly Thr Arg Leu Glu Ile Lys
                100                 105                 110

<210> SEQ ID NO 65
<211> LENGTH: 8
<212> TYPE: PRT
<213> ORGANISM: Homo sapiens

<400> SEQUENCE: 65

Gly Tyr Thr Ser Thr Thr Tyr Gly
1               5

<210> SEQ ID NO 66
<211> LENGTH: 8
<212> TYPE: PRT
<213> ORGANISM: Homo sapiens

<400> SEQUENCE: 66

Ile Asn Pro Tyr Asn Gly Asn Pro
```

```
1               5
```

<210> SEQ ID NO 67
<211> LENGTH: 16
<212> TYPE: PRT
<213> ORGANISM: Homo sapiens

<400> SEQUENCE: 67

```
Ala Arg Asp Gly Trp Gly Gln Gln Leu Val Pro Tyr Tyr Phe Asp Tyr
1               5                   10                  15
```

<210> SEQ ID NO 68
<211> LENGTH: 11
<212> TYPE: PRT
<213> ORGANISM: Homo sapiens

<400> SEQUENCE: 68

```
Gln Ser Leu Leu His Ser Asn Gly Tyr Asn Tyr
1               5                   10
```

<210> SEQ ID NO 69
<211> LENGTH: 3
<212> TYPE: PRT
<213> ORGANISM: Homo sapiens

<400> SEQUENCE: 69

```
Leu Gly Ser
1
```

<210> SEQ ID NO 70
<211> LENGTH: 9
<212> TYPE: PRT
<213> ORGANISM: Homo sapiens

<400> SEQUENCE: 70

```
Met Gln Ala Leu Gln Leu Pro Leu Ala
1               5
```

<210> SEQ ID NO 71
<211> LENGTH: 376
<212> TYPE: DNA
<213> ORGANISM: Homo sapiens

<400> SEQUENCE: 71

```
caggtgcagc tggtggagtc tgggggaggc gtggtccagc ctggggaggtc cctgagactc      60
tcctgtgcag cgtctggatt caccttcagt agttatggca tgcactgggt ccgccaggct     120
ccaggcaagg ggctggagtg ggtggcagtg atatggtatg atggagataa taaatactat     180
ggagactccg tgaagggccg gttcaccatc tccagagaca attccaagaa cactctgttt     240
ctgcaaatga acagcctgag agccgaggac acggctgtgt actactgtgc gaaagacacg     300
gccgaccacg tgactacgt agacctcggg ttttttgacg cctggggcca gggaaccctg     360
gtcaccgtct cctcag                                                     376
```

<210> SEQ ID NO 72
<211> LENGTH: 125
<212> TYPE: PRT
<213> ORGANISM: Homo sapiens

<400> SEQUENCE: 72

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

```
                    20                  25                  30
Gly Met His Trp Val Arg Gln Ala Pro Gly Lys Gly Leu Glu Trp Val
            35                  40                  45

Ala Val Ile Trp Tyr Asp Gly Asp Asn Lys Tyr Tyr Gly Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                85                  90                  95

Ala Lys Asp Thr Ala Asp His Gly Asp Tyr Val Asp Leu Gly Phe Phe
            100                 105                 110

Asp Ala Trp Gly Gln Gly Thr Leu Val Thr Val Ser Ser
            115                 120                 125

<210> SEQ ID NO 73
<211> LENGTH: 322
<212> TYPE: DNA
<213> ORGANISM: Homo sapiens

<400> SEQUENCE: 73
gacatccaga tgacccagtc tccatcttct gtgtctgcat ctgtaggaga cagagtcacc      60
atcacttgtc gggcgagtca ggatgtgagc acctggttag cctggtatca gctgaaacca    120
gggaaagccc ctaagctcct gatctatgct gcatccagtt tgcaaagtgg ggtcccatca    180
aggttcagcg gcagtggatc tgggacagat tcactctcac tgtcagcagc ctgcagcct     240 gaagattttg caacttacta ttgtcaacag gctaacagtt tcccattcac tttcggccct    300
gggaccaaag tggatatcaa ac                                             322

<210> SEQ ID NO 74
<211> LENGTH: 107
<212> TYPE: PRT
<213> ORGANISM: Homo sapiens

<400> SEQUENCE: 74

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Asp Val Ser Thr Trp
            20                  25                  30

Leu Ala Trp Tyr Gln Leu Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Val Ser Ser Leu Gln Pro
 65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 75
<211> LENGTH: 8
<212> TYPE: PRT
<213> ORGANISM: Homo sapiens

<400> SEQUENCE: 75

Gly Phe Thr Phe Ser Ser Tyr Gly
  1               5
```

<210> SEQ ID NO 76
<211> LENGTH: 8
<212> TYPE: PRT
<213> ORGANISM: Homo sapiens

<400> SEQUENCE: 76

Ile Trp Tyr Asp Gly Asp Asn Lys
1               5

<210> SEQ ID NO 77
<211> LENGTH: 18
<212> TYPE: PRT
<213> ORGANISM: Homo sapiens

<400> SEQUENCE: 77

Ala Lys Asp Thr Ala Asp His Gly Asp Tyr Val Asp Leu Gly Phe Phe
1               5                   10                  15

Asp Ala

<210> SEQ ID NO 78
<211> LENGTH: 6
<212> TYPE: PRT
<213> ORGANISM: Homo sapiens

<400> SEQUENCE: 78

Gln Asp Val Ser Thr Trp
1               5

<210> SEQ ID NO 79
<211> LENGTH: 3
<212> TYPE: PRT
<213> ORGANISM: Homo sapiens

<400> SEQUENCE: 79

Ala Ala Ser
1

<210> SEQ ID NO 80
<211> LENGTH: 9
<212> TYPE: PRT
<213> ORGANISM: Homo sapiens

<400> SEQUENCE: 80

Gln Gln Ala Asn Ser Phe Pro Phe Thr
1               5

<210> SEQ ID NO 81
<211> LENGTH: 388
<212> TYPE: DNA
<213> ORGANISM: Homo sapiens

<400> SEQUENCE: 81
gaggtgcagc tggtggagtc tgggggaggc ttggtccagc ctggggaggtc cctgagactc      60 tcctgtgcag cctctggatt cacctttagt gacttttgga tgagctgggt ccgccaggct     120
ccagggaagg ggctggagtg ggtggccaac atagaccaag atggaaatga gagattctat     180
gcggactctg tgaagggccg attcaccatc tccagagaca acgccaagaa ctcactgtat     240
ctgcaaatga ccagcctgag agccgacgac acggccgttt attactgtgc gagagatggg     300
agagagggat atttctatgg ttcggggagt ttttataacc ttaagggtct caattggggc     360
cagggaaccc tgctcaccgt ctcctcag                                        388

<210> SEQ ID NO 82
<211> LENGTH: 129
<212> TYPE: PRT
<213> ORGANISM: Homo sapiens

<400> SEQUENCE: 82

```
Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Ser Asp Phe
            20                  25                  30
Trp Met Ser Trp Val Arg Gln Ala Pro Gly Lys Gly Leu Glu Trp Val
        35                  40                  45
Ala Asn Ile Asp Gln Asp Gly Asn Glu Arg Phe Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Thr Ser Leu Arg Ala Asp Asp Thr Ala Val Tyr Tyr Cys
                85                  90                  95
Ala Arg Asp Gly Arg Glu Gly Tyr Phe Tyr Gly Ser Gly Ser Phe Tyr
            100                 105                 110
Asn Leu Lys Gly Leu Asn Trp Gly Gln Gly Thr Leu Leu Thr Val Ser
        115                 120                 125
Ser
```

<210> SEQ ID NO 83
<211> LENGTH: 331
<212> TYPE: DNA
<213> ORGANISM: Homo sapiens

<400> SEQUENCE: 83

```
cagtctgtgt tgacgcagcc gccctcagtg tctgcggccc caggacagag ggtcaccatc     60
tcctgctctg gaaccagctc aacattggg aaaaattatg tctcctggta ccagcagctc    120
ccaggagcag cccccaaaact cctcatttat gacaatgata agcgaccctc agggattcct    180
gaccgattct ctggctccaa gtctggcacg tcagccaccc tgggcatcac cggactccag    240
actggggacg aggccgatta ttattgcggc acatgggata gcagtctgag tgttgggatg    300
ttcggcggag ggaccaggct gaccgtccta g                                   331
```

<210> SEQ ID NO 84
<211> LENGTH: 110
<212> TYPE: PRT
<213> ORGANISM: Homo sapiens

<400> SEQUENCE: 84

```
Gln Ser Val Leu Thr Gln Pro Pro Ser Val Ser Ala Ala Pro Gly Gln
1               5                   10                  15
Arg Val Thr Ile Ser Cys Ser Gly Thr Ser Ser Asn Ile Gly Lys Asn
            20                  25                  30
Tyr Val Ser Trp Tyr Gln Gln Leu Pro Gly Ala Ala Pro Lys Leu Leu
        35                  40                  45
Ile Tyr Asp Asn Asp Lys Arg Pro Ser Gly Ile Pro Asp Arg Phe Ser
    50                  55                  60
Gly Ser Lys Ser Gly Thr Ser Ala Thr Leu Gly Ile Thr Gly Leu Gln
65                  70                  75                  80
Thr Gly Asp Glu Ala Asp Tyr Tyr Cys Gly Thr Trp Asp Ser Ser Leu
                85                  90                  95
Ser Val Gly Met Phe Gly Gly Gly Thr Arg Leu Thr Val Leu
```

-continued

```
                100             105             110
```

<210> SEQ ID NO 85
<211> LENGTH: 8
<212> TYPE: PRT
<213> ORGANISM: Homo sapiens

<400> SEQUENCE: 85

Gly Phe Thr Phe Ser Asp Phe Trp
1               5

<210> SEQ ID NO 86
<211> LENGTH: 8
<212> TYPE: PRT
<213> ORGANISM: Homo sapiens

<400> SEQUENCE: 86

Ile Asp Gln Asp Gly Asn Glu Arg
1               5

<210> SEQ ID NO 87
<211> LENGTH: 22
<212> TYPE: PRT
<213> ORGANISM: Homo sapiens

<400> SEQUENCE: 87

Ala Arg Asp Gly Arg Glu Gly Tyr Phe Tyr Gly Ser Gly Ser Phe Tyr
1               5                   10                  15

Asn Leu Lys Gly Leu Asn
            20

<210> SEQ ID NO 88
<211> LENGTH: 8
<212> TYPE: PRT
<213> ORGANISM: Homo sapiens

<400> SEQUENCE: 88

Ser Ser Asn Ile Gly Lys Asn Tyr
1               5

<210> SEQ ID NO 89
<211> LENGTH: 3
<212> TYPE: PRT
<213> ORGANISM: Homo sapiens

<400> SEQUENCE: 89

Asp Asn Asp
1

<210> SEQ ID NO 90
<211> LENGTH: 11
<212> TYPE: PRT
<213> ORGANISM: Homo sapiens

<400> SEQUENCE: 90

Gly Thr Trp Asp Ser Ser Leu Ser Val Gly Met
1               5                   10

<210> SEQ ID NO 91
<211> LENGTH: 376
<212> TYPE: DNA
<213> ORGANISM: Homo sapiens

<400> SEQUENCE: 91
gaggtgcaac tggtgcagtc tggagcagag ctgaaaatgc ccggggagtc tctgaagatc      60

```
tcctgtaagg cttctggata cacctttacg aattactgga tcggctgggt gcgccagacg    120
cccgggaaag gcctggaatg gatggggatc atctttcctc ctgactctca aacttcatac    180
agtccgtcct tccaaggcca ggtcaccttc tcagtcgaca actccattag tgttgcctac    240
atacagtgga gtagcctgaa ggcctcggac actgccatat attactgtgc gagatcagga    300 attttttgatt ggtccgcccc ccttgttgaa gcttttgata tttggggcca agggacagtg    360
gtcaccgtct cttcag                                                   376
```

<210> SEQ ID NO 92
<211> LENGTH: 125
<212> TYPE: PRT
<213> ORGANISM: Homo sapiens
<400> SEQUENCE: 92

```
Glu Val Gln Leu Val Gln Ser Gly Ala Glu Leu Lys Met Pro Gly Glu
1               5                   10                  15

Ser Leu Lys Ile Ser Cys Lys Ala Ser Gly Tyr Thr Phe Thr Asn Tyr
            20                  25                  30

Trp Ile Gly Trp Val Arg Gln Thr Pro Gly Lys Gly Leu Glu Trp Met
        35                  40                  45

Gly Ile Ile Phe Pro Pro Asp Ser Gln Thr Ser Tyr Ser Pro Ser Phe
    50                  55                  60

Gln Gly Gln Val Thr Phe Ser Val Asp Asn Ser Ile Ser Val Ala Tyr
65                  70                  75                  80

Ile Gln Trp Ser Ser Leu Lys Ala Ser Asp Thr Ala Ile Tyr Tyr Cys
                85                  90                  95

Ala Arg Ser Gly Ile Phe Asp Trp Ser Ala Pro Leu Val Glu Ala Phe
            100                 105                 110

Asp Ile Trp Gly Gln Gly Thr Val Val Thr Val Ser Ser
        115                 120                 125
```

<210> SEQ ID NO 93
<211> LENGTH: 322
<212> TYPE: DNA
<213> ORGANISM: Homo sapiens
<400> SEQUENCE: 93

```
gacatccagt tgacccagtc tccatccttc ctgtctgcat ctgtgggaga cggagtcacc    60
atcacttgcc gggccagtca ggacatttac atttatttag cctggtatca gcaaaaaccg    120
gggaaagccc ctaaactcct gatctatgct gcctccactc tgcagggtgg ggtcccatca    180
aggttcagcg gcagtggatc tgggacagaa ttcactctca caatcaacaa cctgcagcct    240
gaggattttg caacttattt ctgtcagcaa cttaatggct accccctcac tttcggcgga    300
gggaccaagg tggagatcaa ac                                            322
```

<210> SEQ ID NO 94
<211> LENGTH: 107
<212> TYPE: PRT
<213> ORGANISM: Homo sapiens
<400> SEQUENCE: 94

```
Asp Ile Gln Leu Thr Gln Ser Pro Ser Phe Leu Ser Ala Ser Val Gly
1               5                   10                  15

Asp Gly Val Thr Ile Thr Cys Arg Ala Ser Gln Asp Ile Tyr Ile Tyr
            20                  25                  30

Leu Ala Trp Tyr Gln Gln Lys Pro Gly Lys Ala Pro Lys Leu Leu Ile
```

```
                35                  40                  45
Tyr Ala Ala Ser Thr Leu Gln Gly Gly Val Pro Ser Arg Phe Ser Gly
            50                  55                  60

Ser Gly Ser Gly Thr Glu Phe Thr Leu Thr Ile Asn Asn Leu Gln Pro
65                  70                  75                  80

Glu Asp Phe Ala Thr Tyr Phe Cys Gln Gln Leu Asn Gly Tyr Pro Leu
                85                  90                  95

Thr Phe Gly Gly Gly Thr Lys Val Glu Ile Lys
            100                 105

<210> SEQ ID NO 95
<211> LENGTH: 8
<212> TYPE: PRT
<213> ORGANISM: Homo sapiens

<400> SEQUENCE: 95

Gly Tyr Thr Phe Thr Asn Tyr Trp
1               5

<210> SEQ ID NO 96
<211> LENGTH: 8
<212> TYPE: PRT
<213> ORGANISM: Homo sapiens

<400> SEQUENCE: 96

Ile Phe Pro Pro Asp Ser Gln Thr
1               5

<210> SEQ ID NO 97
<211> LENGTH: 18
<212> TYPE: PRT
<213> ORGANISM: Homo sapiens

<400> SEQUENCE: 97

Ala Arg Ser Gly Ile Phe Asp Trp Ser Ala Pro Leu Val Glu Ala Phe
1               5                   10                  15

Asp Ile

<210> SEQ ID NO 98
<211> LENGTH: 6
<212> TYPE: PRT
<213> ORGANISM: Homo sapiens

<400> SEQUENCE: 98

Gln Asp Ile Tyr Ile Tyr
1               5

<210> SEQ ID NO 99
<211> LENGTH: 3
<212> TYPE: PRT
<213> ORGANISM: Homo sapiens

<400> SEQUENCE: 99

Ala Ala Ser
1

<210> SEQ ID NO 100
<211> LENGTH: 9
<212> TYPE: PRT
<213> ORGANISM: Homo sapiens

<400> SEQUENCE: 100

Gln Gln Leu Asn Gly Tyr Pro Leu Thr
```

<210> SEQ ID NO 101
<211> LENGTH: 376
<212> TYPE: DNA
<213> ORGANISM: Homo sapiens

<400> SEQUENCE: 101

```
gaggtgcagc tggtgcagtc tggagcagag gtgaaaaagc ccggggagtc tctgaagatc      60
tcctgtaagg gttctggata cagttttagc gattactgga tcggctgggt gcgccagatg     120
cccggggaag gcctggaatg gatggggatc atctatcctg ctagttctga atcagatac      180
agcccgtcct ccagggcct  ggtcaccatc tcagccgaca gtccatcaa caccgcctcc      240
ctgcagtgga gcagcctgaa ggcctcggac accgccatct attactgcgc gagacatgcc      300
tcttgtagtg ctcgtagctg ttattggggg cccgttgact actggggcca gggaaccctg      360
gtcaccgtct cctcag                                                      376
```

<210> SEQ ID NO 102
<211> LENGTH: 125
<212> TYPE: PRT
<213> ORGANISM: Homo sapiens

<400> SEQUENCE: 102

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asp Tyr
                20                  25                  30
Trp Ile Gly Trp Val Arg Gln Met Pro Gly Glu Gly Leu Glu Trp Met
            35                  40                  45
Gly Ile Ile Tyr Pro Ala Ser Ser Glu Ile Arg Tyr Ser Pro Ser Phe
        50                  55                  60
Gln Gly Leu Val Thr Ile Ser Ala Asp Lys Ser Ile Asn Thr Ala Ser
65                  70                  75                  80
Leu Gln Trp Ser Ser Leu Lys Ala Ser Asp Thr Ala Ile Tyr Tyr Cys
                85                  90                  95
Ala Arg His Ala Ser Cys Ser Ala Arg Ser Cys Tyr Trp Gly Pro Val
                100                 105                 110
Asp Tyr Trp Gly Gln Gly Thr Leu Val Thr Val Ser Ser
            115                 120                 125

<210> SEQ ID NO 103
<211> LENGTH: 337
<212> TYPE: DNA
<213> ORGANISM: Homo sapiens

<400> SEQUENCE: 103

```
gatattgtga tgactcagtc tccactctcc ctgcccgtct cccctggaga gccggcctcc      60
atctcctgca ggtctagtca gagcctccta catggtaatg gatacaacta tttggattgg     120
tacctgcaga agccagggca gtctccacgc ctcctgatct atttgggttc aatcgggcc      180
tccggggtcc ctgataggtt cagtggcagt ggatcaggca cagattttac actgaaaatc      240
agcagagtgg aggctgaaga tgttggggtt tattactgca tgcaagctct acaaactccg      300
```
ctcactttcg gcggagggac caaggtggag atcaaac    337

<210> SEQ ID NO 104
<211> LENGTH: 112
<212> TYPE: PRT
<213> ORGANISM: Homo sapiens

<400> SEQUENCE: 104

Asp Ile Val Met Thr Gln Ser Pro Leu Ser Leu Pro Val Ser Pro Gly
1               5                   10                  15

Glu Pro Ala Ser Ile Ser Cys Arg Ser Ser Gln Ser Leu Leu His Gly
            20                  25                  30

Asn Gly Tyr Asn Tyr Leu Asp Trp Tyr Leu Gln Lys Pro Gly Gln Ser
        35                  40                  45

Pro Arg Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 105
<211> LENGTH: 8
<212> TYPE: PRT
<213> ORGANISM: Homo sapiens

<400> SEQUENCE: 105

Gly Tyr Ser Phe Ser Asp Tyr Trp
1               5

<210> SEQ ID NO 106
<211> LENGTH: 8
<212> TYPE: PRT
<213> ORGANISM: Homo sapiens

<400> SEQUENCE: 106

Ile Tyr Pro Ala Ser Ser Glu Ile
1               5

<210> SEQ ID NO 107
<211> LENGTH: 18
<212> TYPE: PRT
<213> ORGANISM: Homo sapiens

<400> SEQUENCE: 107

Ala Arg His Ala Ser Cys Ser Ala Arg Ser Cys Tyr Trp Gly Pro Val
1               5                   10                  15

Asp Tyr

<210> SEQ ID NO 108
<211> LENGTH: 11
<212> TYPE: PRT
<213> ORGANISM: Homo sapiens

<400> SEQUENCE: 108

Gln Ser Leu Leu His Gly Asn Gly Tyr Asn Tyr
1               5                   10

<210> SEQ ID NO 109
<211> LENGTH: 3

```
<212> TYPE: PRT
<213> ORGANISM: Homo sapiens

<400> SEQUENCE: 109

Leu Gly Ser
1

<210> SEQ ID NO 110
<211> LENGTH: 9
<212> TYPE: PRT
<213> ORGANISM: Homo sapiens

<400> SEQUENCE: 110

Met Gln Ala Leu Gln Thr Pro Leu Thr
1               5
```